United States Patent
Houriet, Jr. et al.

(10) Patent No.: US 7,657,446 B1
(45) Date of Patent: Feb. 2, 2010

(54) AUTOMATED IDENTIFICATION OF TASKS THAT MUST BE COMPLETED BEFORE A CLINICAL TRIAL DATABASE CAN BE LOCKED

(75) Inventors: John W. Houriet, Jr., Yardley, PA (US); Jianbo Peng, Drexel Hill, PA (US)

(73) Assignee: Numoda Technologies, Inc., Philadelphia, PA (US)

( * ) Notice: Subject to any disclaimer, the term of this patent is extended or adjusted under 35 U.S.C. 154(b) by 0 days.

(21) Appl. No.: 12/416,747

(22) Filed: Apr. 1, 2009

Related U.S. Application Data

(60) Provisional application No. 61/091,142, filed on Aug. 22, 2008.

(51) Int. Cl.
*G06Q 50/00* (2006.01)
(52) U.S. Cl. .................. 705/3; 707/8; 707/9; 705/2; 600/300
(58) Field of Classification Search .......... 705/2–3; 707/3, 8–10, 101, 104.1; 600/300
See application file for complete search history.

(56) References Cited

U.S. PATENT DOCUMENTS

| | | | |
|---|---|---|---|
| 7,054,823 B1 | 5/2006 | Briegs et al. | |
| 7,444,293 B1 | 10/2008 | Kahn et al. | |
| 2003/0065669 A1 | 4/2003 | Kahn et al. | |
| 2004/0093240 A1 | 5/2004 | Shah | |
| 2004/0249664 A1* | 12/2004 | Broverman et al. | 705/2 |
| 2005/0075832 A1* | 4/2005 | Ikeguchi et al. | 702/179 |
| 2005/0149852 A1 | 7/2005 | Bleicher et al. | |
| 2005/0165829 A1* | 7/2005 | Varasano | 707/102 |
| 2005/0210026 A1 | 9/2005 | Wood | |
| 2006/0015433 A1 | 1/2006 | Arnott et al. | |
| 2006/0281122 A1* | 12/2006 | Bryant et al. | 435/6 |
| 2008/0010089 A1* | 1/2008 | DiMaggio et al. | 705/2 |
| 2008/0046469 A1 | 2/2008 | Ikeguchi et al. | |
| 2008/0086387 A1 | 4/2008 | O'Rourke et al. | |
| 2008/0162372 A1 | 7/2008 | Margolis et al. | |
| 2008/0270181 A1 | 10/2008 | Rosenberg | |

FOREIGN PATENT DOCUMENTS

WO    0193178 A2    12/2001

OTHER PUBLICATIONS

TrialMaster brochure, OmniComm Systems, Inc., Copyright 2007, downloaded from website: http://www.omnicomm.com/3eClinicalSolutions/pdfs/TrialMaster+v4[1].0+Data+Sheet.PDF, 9 pages.

(Continued)

*Primary Examiner*—Gerald J. O'Connor
*Assistant Examiner*—Sind Phongsvirajati
(74) *Attorney, Agent, or Firm*—Panitch Schwarze Belisario & Nadel LLP

(57) ABSTRACT

Management of a database lock for a clinical trial study is provided. A database is provided that includes clinical trial data and the status of the data for a plurality of patients. Lock criteria is defined for the study from a plurality of selectable subsets of the clinical trial data. A processor automatically generates a list of tasks that must occur to achieve the lock defined by the lock criteria using the clinical trial data and the status of the data.

19 Claims, 33 Drawing Sheets

OTHER PUBLICATIONS

CleanWEB• brochure, Telemedicine Technologies S.A., Copyright 2003, downloaded from website: http://cleanweb.tentelemed.con/docs/leaflet-uk.pdf, 5 pages.

T. Ganslandt et al. "A Flexible Repository for Clinical Trial Data Based on an Entity-Attribute-Value Model," downloaded from website: http://www2.amia.org/pubs/symposia/D005543.PDF, publication date is unknown, 4 pages.

Nivedan Prakash, "Technology-driven clinical trials," downloaded from website: http://www.expresscomputeronline.com/20081201/management01.shtml, Dec. 1, 2008, 5 pages.

CleanWEB™ brochure, Telemedicine Technologies S.A., Copyright 2003, downloaded from website: http://cleanweb.tentelemed.con/docs/leaflet-uk.pdf, 5 pages.

T. Ganslandt et al. "A Flexible Repository for Clinical Trial Data Based on an Entity-Attribute-Value Model," downloaded from website: http://www2.amia.org/pubs/symposia/D005543.PDF, publication date is unknown, 4 pages.

Nivedan Prakash, "Technology-driven clinical trials," downloaded from website: http://www.expresscomputeronline.com/20081201/management01.shtml, Dec. 1, 2008, 5 pages.

* cited by examiner

Figure 5

Lock Criteria interface
1. Criteria Name _____
2. CRFs
   ☒ Informed Consent Demographics
   ☒ Physical Examination
   ☒ Medical History
   ☒ Inclusion Exclusion
   ☒ Laboratory Collection
   ☒ Vital Signs
   ☒ Dosing Log
   ☐ Coded Adverse Serious Event
   ☐ Coded Concomitant Medications and Therapies
3. Time points:
   ☒ V1
   ☒ V2
   ☒ V3
   ☒ V4
   ☒ V5
   ☐ Specific Date 6/12/2008
4. Patient Type:
   ☐ Screened
   ☐ Screen Failed
   ☒ Enrolled
   ☒ Discontinued
   ☐ Completed
   ☐ Open Label Screened
   ☐ Open Label Enrolled
   ☐ Open Label Discontinued
   ☐ Open Label Completed

Figure 12A

Version 1.0.0
Posted by:

Posted date: 02 06 2008 15 06 54

Soft Lock Summary

| Site | # Enrolled | # Done | CRFc Completed | CRFs Locked | CRFs Inc/Pending | CRFs Queried | Visit Queries | # Queries |
|---|---|---|---|---|---|---|---|---|
| 10 | 19 | 17 | 281 | 280 | 0 | 1 | 0 | 2 |
| 11 | 18 | 18 | 270 | 270 | 0 | 0 | 0 | 0 |
| 12 | 5 | 5 | 71 | 71 | 0 | 0 | 0 | 0 |
| 13 | 29 | 29 | 416 | 416 | 0 | 1 | 0 | 0 |
| 14 | 12 | 11 | 180 | 179 | 0 | 0 | 0 | 1 |
| 15 | 12 | 11 | 176 | 176 | 0 | 0 | 0 | 1 |
| 16 | 10 | 10 | 150 | 150 | 0 | 0 | 0 | 0 |
| 17 | 5 | 5 | 64 | 64 | 0 | 0 | 0 | 0 |
| 18 | 2 | 2 | 27 | 27 | 0 | 0 | 0 | 0 |
| 19 | 11 | 11 | 157 | 157 | 0 | 0 | 0 | 0 |
| 22 | 4 | 4 | 60 | 60 | 0 | 0 | 0 | 0 |
| 23 | 8 | 8 | 113 | 113 | 0 | 0 | 0 | 0 |
| 25 | 4 | 4 | 60 | 60 | 0 | 0 | 0 | 0 |
| 30 | 2 | 2 | 30 | 30 | 0 | 0 | 0 | 0 |
| 31 | 6 | 3 | 79 | 76 | 0 | 2 | 0 | 2 |
| 32 | 15 | 15 | 225 | 225 | 0 | 0 | 0 | 0 |
| 33 | 4 | 4 | 60 | 60 | 0 | 0 | 0 | 0 |
| 34 | 8 | 8 | 120 | 120 | 0 | 0 | 0 | 0 |
| 35 | 6 | 6 | 86 | 86 | 0 | 0 | 0 | 0 |
| 36 | 8 | 8 | 120 | 120 | 0 | 0 | 0 | 0 |

Study Summary
Safety
Monitoring
Data Management
Administration
Study Documents

Log Off

Figure 12B

| Study Summary | | | | | | | | |
|---|---|---|---|---|---|---|---|---|
| Safety | Site | # Enrolled | # Done | CRFs Completed | CRFs Locked | Record # CRFs Inc/Pending | CRFs Queried | Visit Queries | # Queries |
| Monitoring | 10 | 19 | 17 | 281 | 280 | 0 | 1 | 0 | 2 |
| Data Management | 11 | 18 | 18 | 270 | 270 | 0 | 0 | 0 | 0 |
| Administration | 12 | 5 | 5 | 71 | 71 | 0 | 0 | 0 | 0 |
| Study Documents | 13 | 29 | 29 | 416 | 416 | 0 | 0 | 0 | 0 |
| Log Off | 14 | 12 | 11 | 180 | 179 | 0 | 1 | 0 | 1 |
| | 15 | 12 | 11 | 176 | 176 | 0 | 0 | 0 | 1 |
| | 16 | 10 | 10 | 150 | 150 | 0 | 0 | 0 | 0 |
| | 17 | 5 | 5 | 64 | 64 | 0 | 0 | 0 | 0 |
| | 18 | 2 | 2 | 27 | 27 | 0 | 0 | 0 | 0 |
| | 19 | 11 | 11 | 157 | 157 | 0 | 0 | 0 | 0 |
| | 22 | 4 | 4 | 60 | 60 | 0 | 0 | 0 | 0 |
| | 23 | 8 | 8 | 113 | 113 | 0 | 0 | 0 | 0 |
| | 25 | 4 | 4 | 60 | 60 | 0 | 0 | 0 | 0 |
| | 30 | 2 | 2 | 30 | 30 | 0 | 0 | 0 | 0 |
| | 31 | 6 | 3 | 79 | 76 | 0 | 2 | 0 | 2 |
| | 43 | 1 | 1 | 15 | 15 | 0 | 0 | 0 | 0 |
| | 44 | 3 | 3 | 38 | 38 | 0 | 0 | 0 | 0 |
| | 45 | 0 | 0 | 0 | 0 | 0 | 0 | 0 | 0 |
| | 46 | 0 | 0 | 0 | 0 | 0 | 0 | 0 | 0 |
| | 47 | 10 | 10 | 149 | 149 | 0 | 0 | 0 | 0 |
| | 48 | 0 | 0 | 0 | 0 | 0 | 0 | 0 | 0 |
| | 49 | 2 | 2 | 23 | 23 | 0 | 0 | 0 | 0 |
| | 50 | 0 | 0 | 0 | 0 | 0 | 0 | 0 | 0 |
| | 53 | 1 | 1 | 14 | 14 | 0 | 0 | 0 | 0 |
| | 61 | 1 | 1 | 15 | 15 | 0 | 0 | 0 | 0 |
| | 62 | 2 | 2 | 30 | 30 | 0 | 0 | 0 | 0 |
| | 65 | 0 | 0 | 0 | 0 | 0 | 0 | 0 | 0 |
| | Total | 167 | 160 | 2418 | 2413 | 0 | 4 | 0 | 6 |

Figure 13

| | 1 | | 2 | 3 | 4 Record # | | | | |
|---|---|---|---|---|---|---|---|---|---|
| | Patient | Status | PAN Therapy | CRF's Completed | CRF's Locked | CRF's in Pending | CRF's Queried | Visit Queries | # Queries |
| | 12001 | C (Done) | Y | 15 15 | 15 | 0 | 0 | 0 | 0 |
| | 12003 | C (Done) | Y | 15 15 | 15 | 0 | 0 | 0 | 0 |
| | 12004 | C (Done) | Y | 15 15 | 15 | 0 | 0 | 0 | 0 |
| | 12005 | C (Done) | Y | 15 15 | 15 | 0 | 0 | 0 | 0 |
| | 12006 | C (Done) | Y | 15 15 | 15 | 0 | 0 | 0 | 0 |
| | 12007 | C (Done) | Y | 15 15 | 15 | 0 | 0 | 0 | 0 |
| | 12008 | C (Done) | Y | 15 15 | 15 | 0 | 0 | 0 | 0 |
| | 12009 | C (Done) | Y | 15 15 | 15 | 0 | 0 | 0 | 0 |
| | 12010 | C (Done) | Y | 15 15 | 15 | 0 | 0 | 0 | 0 |
| | 12011 | C (Done) | Y | 15 15 | 15 | 0 | 0 | 0 | 0 |
| | 12012 | C (Done) | Y | 15 15 | 15 | 0 | 0 | 0 | 0 |
| | 12013 | D | Y | 15 15 | 10 | 0 | 1 | 0 | 1 |
| | 12014 | C (Done) | Y | 15 15 | 15 | 0 | 0 | 0 | 0 |
| | 12015 | C (Done) | Y | 15 15 | 15 | 0 | 0 | 0 | 0 |
| | 12016 | C (Done) | Y | 15 15 | 15 | 0 | 0 | 0 | 0 |
| | 12017 | C | Y | 15 15 | 15 | 0 | 0 | 0 | 1 |
| | 12018 | C (Done) | Y | 15 15 | 15 | 0 | 0 | 0 | 0 |
| | 12019 | C (Done) | Y | 15 15 | 15 | 0 | 0 | 0 | 0 |
| | 12020 | C (Done) | Y | 15 15 | 15 | 0 | 0 | 0 | 0 |

(Tasks remaining at the site) 9

Study Summary
Safety
Monitoring
Data Management
Administration
Study Documents

Log Off — 10

Figure 15A

Soft Lock Detail of 10001

| Form\Visit | BL/ V1 | V2 | Wk 2 Ph 1 | Wk 4 Ph 2 | Wk 6 V3 | Wk 8 Ph 3 | Wk 10 Ph 4 | V 4 | Wk 12 V5 |
|---|---|---|---|---|---|---|---|---|---|
| Informed Consent/Demographics | L | -- | -- | -- | -- | -- | -- | -- | -- |
| Inclusion/Exclusion | L | -- | -- | -- | -- | -- | -- | -- | L |
| 6MWT/Borg Dyspnea Score | L | L | -- | -- | L | -- | -- | L | L |
| NYHA Functional Assessment | L | -- | -- | -- | L | -- | -- | -- | L |
| Study Medication Dispensed/Returned | -- | L | -- | -- | L | -- | -- | -- | L |
| Study Termination | -- | -- | -- | -- | -- | -- | -- | -- | L |
| Early Trial Termination | | | | | L | | | | |
| PAH Worksheet | | | | | | | | | |

L Locked  C Completed  I Incompleted/Pending

Q Queried  ☐ Not Done  ☐ -- Not Required

View Queries  Visit Queries

COTHER -- related to approved therapies (Randomization Date: 28 JUN 2005)

| CONRX | CONRX V | CTIND_V | CTDOS EC | CTUN IT | CTROU TE | CTFR EQ | CTRO M_C | CTT O_C | CTON GO | CMATCC DE | CMATCTXT | CMWHO TXT | COMRAN DATE |
|---|---|---|---|---|---|---|---|---|---|---|---|---|---|
| TRACLEER | TRACLEER | PULMONARY ARTERIAL HYPERTENSION | 125 | MG | PO | BID | 12 MAR 2002 | | YES | C02KX | OTHER ANTIHYPERTENSIVES | Tracleer | EARLY |

Figure 15B

Soft Lock Detail of 10013

| Form\Visit | BL V1 | V2 | Wk 2 Ph 1 | Wk 4 Ph 2 | Wk 6 V3 | Wk 8 Ph 3 | Wk 10 Ph 4 | V 4 | Wk 12 V5 |
|---|---|---|---|---|---|---|---|---|---|
| Informed Consent/Demographics | L | -- | -- | -- | -- | -- | -- | -- | -- |
| Inclusion/Exclusion | L | -- | -- | -- | -- | -- | -- | -- | -- |
| 6MWT/Borg Dyspnea Score | L | L | -- | -- | L | -- | -- | -- | -- |
| NYHA Functional Assessment | L | -- | -- | -- | L | -- | -- | -- | |
| Study Medication Dispensed/Returned | -- | L | -- | -- | L | -- | -- | -- | |
| Study Termination | | | | | | | | | |
| Early Trial Termination | | | | | L | | | | |
| PAH Worksheet | | | | | L | | | | |

L Locked    C Completed    I Incompleted/Pending

Q Queried    Not Done    -- Not Required

View Queries (0 Visit Queries)

COTHER -- related to approved therapies (Randomization Date: 17 AUG 2006)

| CONRX | CONRX_V | CTIND_V | CTDOSEC | CTUNIT | CTROUTE | CTFREQ | CTFROM_C | CTTO_C | CTONGO | CTMATCCDE | CTMATCTXT | CMWHOTXT | COMRANDATE |
|---|---|---|---|---|---|---|---|---|---|---|---|---|---|
| SILDENAFIL | SILDENAFIL | PULMONARY ARTERIAL HYPERTENSION | 80 | MG | PO | TID | 03 MAY 2003 | | YES | G04BE | Drugs used in erectile dysfunction | Sildenafil | EARLY |

Figure 19

| Site | # Enrolled | # Done | CRFs Completed | CRFs Locked | CRFs Inc/Pending | CRFs Queried | Log (Lock Comp) | Visit Queries | # Queries | # Enrolled | # Done | CRFc Completed | CRFs Locked | CRFs Inc/Pending | CRFs Queried | Visit Queries | # Queries |
|---|---|---|---|---|---|---|---|---|---|---|---|---|---|---|---|---|---|
| | | | | Blinded - Record # | | | | | | | | | Open Label to June 1 2008 - Record # | | | | |
| 10 | 19 | 0 | 799 | 729 | 1 | 25 | 333842 | 0 | 84 | 18 | 17 | 936 | 774 | 9 | 30 | 0 | 38 |
| 11 | 18 | 13 | 763 | 764 | 1 | 1 | 382412 | 0 | 3 | 18 | 14 | 842 | 860 | 2 | 0 | 0 | 0 |
| 12 | 5 | 1 | 199 | 199 | 0 | 0 | 188214 | 0 | 1 | 2 | 1 | 142 | 102 | 1 | 0 | 0 | 1 |
| 13 | 29 | 5 | 1141 | 1129 | 0 | 13 | 2821142 | 0 | 2 | 25 | 11 | 1055 | 1059 | 0 | 9 | 0 | 9 |
| 14 | 12 | 0 | 515 | 506 | 0 | 1 | 28248 | 0 | 41 | 12 | 0 | 613 | 585 | 11 | 10 | 0 | 14 |
| 15 | 12 | 0 | 491 | 473 | 7 | 2 | 50295 | 0 | 28 | 9 | 0 | 429 | 275 | 4 | 35 | 0 | 41 |
| 16 | 10 | 7 | 430 | 430 | 0 | 0 | 229252 | 0 | 2 | 10 | 8 | 439 | 439 | 1 | 0 | 0 | 0 |
| 17 | 5 | 0 | 173 | 172 | 0 | 3 | 12195 | 0 | 7 | 3 | 1 | 87 | 85 | 0 | 2 | 0 | 2 |
| 18 | 2 | 1 | 74 | 72 | 0 | 2 | 4747 | 0 | 3 | 1 | 1 | 26 | 26 | 0 | 0 | 0 | 0 |
| 19 | 11 | 4 | 436 | 428 | 2 | 15 | 323347 | 0 | 44 | 9 | 2 | 240 | 227 | 5 | 2 | 0 | 5 |
| 22 | 4 | 2 | 172 | 172 | 0 | 0 | 125126 | 0 | 4 | 4 | 2 | 64 | 62 | 0 | 2 | 0 | 2 |
| 23 | 8 | 1 | 313 | 311 | 1 | 5 | 221252 | 0 | 6 | 7 | 4 | 189 | 186 | 4 | 0 | 0 | 0 |
| 25 | 4 | 2 | 172 | 172 | 1 | 0 | 190193 | 0 | 1 | 4 | 4 | 85 | 85 | 0 | 0 | 0 | 0 |
| 44 | 3 | 3 | 104 | 104 | 0 | 0 | 2222 | 0 | 0 | 2 | 2 | 23 | 23 | 0 | 0 | 0 | 0 |
| 45 | 0 | 0 | 0 | 0 | 0 | 0 | 0 | 0 | 0 | 0 | 0 | 0 | 0 | 0 | 0 | 0 | 0 |
| 46 | 0 | 0 | 0 | 0 | 0 | 0 | 0 | 0 | 0 | 0 | 0 | 0 | 0 | 0 | 0 | 0 | 0 |
| 47 | 10 | 10 | 424 | 423 | 0 | 0 | 219219 | 0 | 0 | 9 | 9 | 204 | 204 | 0 | 0 | 0 | 0 |
| 48 | 0 | 0 | 0 | 0 | 0 | 0 | 0 | 0 | 0 | 0 | 0 | 0 | 0 | 0 | 0 | 0 | 0 |
| 49 | 2 | 2 | 29 | 29 | 0 | 0 | 3436 | 0 | 0 | 1 | 1 | 34 | 36 | 0 | 0 | 0 | 0 |
| 50 | 0 | 0 | 0 | 0 | 0 | 0 | 0 | 0 | 0 | 0 | 0 | 0 | 0 | 0 | 0 | 0 | 0 |
| 53 | 1 | 1 | 37 | 37 | 0 | 0 | 155 | 0 | 0 | 1 | 1 | 14 | 14 | 0 | 0 | 0 | 0 |
| Total | 155 | 52 | 6272 | 6150 | 13 | 67 | | 0 | 226 | 135 | 78 | 5433 | 5042 | 37 | 90 | 0 | 112 |

Figure 20

| Patient | Status | Blinded -- Record # | | | | | | Hard Lock Detail Status | Open Label to Jan 1 2008 -- Record # | | | |
|---|---|---|---|---|---|---|---|---|---|---|---|---|
| | | CRFs Complete | CRFs Locked | CRFs Inc./Pending | CRFs Queried | Log (Lock/Cmpt) | Visit Queries | # Queries | | CRFs Complete | CRFs Locked | CRFs Inc./Pending | CRFs Queried | Visit Queries | # Queries |
| 10001 | C(Done) | 43/43 | 43 | 0 | 0 | 62/62 | 0 | 0 | (Done) | 96 | 96 | 0 | 0 | 0 |
| 10003 | C(Done) | 43/43 | 43 | 0 | 0 | 24/24 | 0 | 0 | D(Done) | 27 | 27 | 0 | 0 | 0 |
| 10004 | C(Done) | 43/43 | 43 | 0 | 0 | 91/91 | 0 | 0 | (Done) | 96 | 96 | 0 | 0 | 0 |
| 10005 | C(Done) | 43/43 | 43 | 0 | 0 | 56/56 | 0 | 0 | (Done) | 96 | 96 | 0 | 0 | 0 |
| 10006 | C(Done) | 43/43 | 43 | 0 | 0 | 51/51 | 0 | 0 | D(Done) | 27 | 27 | 0 | 0 | 0 |
| 10007 | C(Done) | 43/43 | 43 | 0 | 0 | 27/27 | 0 | 0 | D(Done) | 27 | 27 | 0 | 0 | 0 |
| 10008 | C(Done) | 43/43 | 43 | 0 | 0 | 22/22 | 0 | 0 | D(Done) | 17 | 17 | 0 | 0 | 0 |
| 10009 | C(Done) | 43/43 | 43 | 0 | 0 | 51/51 | 0 | 0 | (Done) | 76 | 76 | 0 | 0 | 0 |
| 10010 | C(Done) | 43/43 | 43 | 0 | 0 | 38/38 | 0 | 0 | (Done) | 76 | 76 | 0 | 0 | 0 |
| 10011 | C(Done) | 43/43 | 43 | 0 | 0 | 60/60 | 0 | 0 | (Done) | 76 | 76 | 0 | 0 | 0 |
| 10012 | C | 43/43 | 43 | 0 | 0 | 37/39 | 0 | 0 | (Done) | 76 | 76 | 0 | 0 | 0 |
| 10013 | D(Done) | 26/26 | 26 | 0 | 0 | 27/27 | 0 | 0 | | 0 | 0 | 0 | 0 | 0 |
| 10014 | C(Done) | 43/43 | 43 | 0 | 0 | 110/110 | 0 | 0 | D(Done) | 37 | 37 | 0 | 0 | 0 |
| 10015 | C(Done) | 43/43 | 43 | 0 | 0 | 21/21 | 0 | 1 | D(Done) | 47 | 47 | 0 | 0 | 0 |
| 10016 | C(Done) | 43/43 | 43 | 0 | 0 | 42/42 | 0 | 0 | (Done) | 46 | 46 | 0 | 0 | 0 |
| 10017 | C | 43/43 | 43 | 0 | 0 | 28/29 | 0 | 0 | (Done) | 46 | 46 | 0 | 0 | 0 |
| 10018 | C(Done) | 43/43 | 43 | 0 | 0 | 13/13 | 0 | 0 | (Done) | 26 | 26 | 0 | 0 | 0 |
| 10019 | C(Done) | 43/43 | 43 | 0 | 0 | 41/41 | 0 | 0 | (Done) | 26 | 26 | 0 | 0 | 0 |
| 10020 | C(Done) | 43/43 | 43 | 0 | 0 | 59/59 | 0 | 0 | (Done) | 26 | 26 | 0 | 0 | 0 |

[Tasks remaining at this site -- Blinded] [Tasks remaining at this site -- Open Label]

Status
C -- Patient completed study
D -- Patient discontinued study
(Done) -- Patient complete and lock all required eCRFs

Figure 21

| Blinded | | | |
|---|---|---|---|
| Patient | | Task | |
| 10001 | Laboratory Collection CRF of Wk 12 V5 needs to be locked | | |
| 10001 | Query for Wk 12 V5 Laboratory Collection CRF needs a response from site. The CRF will need to be locked once the query has been closed and acknowledged | Please verify if Neutrophils were resulted. If yes, please enter result into the lab CRF page (DB v5, 9/21/05) | |
| 10003 | Laboratory Collection CRF of Wk 6 V5 needs to be locked | | |
| 10003 | Laboratory Collection CRF of Wk 12 V5 needs to be locked | | |
| 10003 | Query for Wk 6 v5 Laboratory Collection CRF needs a response from site. The CRF will need to be locked once the query has been closed and acknowledged | Verify Chloride result of 10.0. Also, verify unit of measurement is correct? Please enter reply into this query and make appropriate changes into the CRf (DB v3, 8/25/05) | |
| 10003 | Query for Wk 6 v5 Laboratory Collection CRF needs a response from site. The CRF will need to be locked once the query has been closed and acknowledged | Verify platelet result of 6.0. Also, verify unit of measurement (DB v3, 8/25/05 | |
| 10003 | Query for Wk 12 v5 Laboratory Collection CRF needs a response from site. The CRF will need to be locked once the query has been closed and acknowledged | Verify neutrophils were resulted. If yes, please enter result into CRF (DB v5, 10/5/05) | |
| 10003 | Adverse Serious Events CRF needs to be locked | | |

Study Summary
Safety
Monitoring
Data Management
Administration
Study Documents
Log Off

Figure 22

Open Label

| Patient | Task | |
|---|---|---|
| 10001 | 6MWT Sorg Dyspnea Score CRF of OL, V3 needs to be locked | |
| 10001 | 6MWT Sorg Dyspnea ScoreCRF of OL, V9 needs to be locked | |
| 10001 | 6MWT Sorg Dyspnea Score CRF of OL, V10 needs to be locked | |
| 10001 | Signs and Symptoms of PAN CRF of OL V7 needs to be locked | |
| 10001 | Open Label Study Med CRF of OL, V3 needs to be locked | |
| 10003 | Query for OL, V9 MWT Sorg Dyspnea Score CRF needs a response from site. The CRF will need to be locked once the query has been closed and acknowledged | Please verify whether the 6MWT was performed outside of the BOS window (OL, v9) |
| 10001 | Query for OL, V10 MWT Sorg Dyspnea Score CRF needs a response from site. The CRF will need to be locked once the query has been closed and acknowledged | Please verify time of bosentan administration |
| 10001 | Query for OL, V7 Signs and Symptoms of PAN CRF needs a response from site. The CRF will need to be locked once the query has been closed and acknowledged | Please verify presence of heave, source states present, CRF=absent. |
| 10001 | Query for OL, V7 Open Label Study Med CRF needs a response from site. The CRF will need to be locked once the query has been closed and acknowledged | Please verify number of amps returned at this visit. Source = 1,CRF = 16 (OL, v5, 5/1/07) |

Figure 23A

Blinded Study

| Form\Visit | BL/ V 1 | V 2 | Wk 2 Ph 1 | Wk 4 Ph 2 | Wk 6 V 3 | Wk 8 Ph 3 | Wk 10 Ph 4 | V 4 | Wk 12 V5 |
|---|---|---|---|---|---|---|---|---|---|
| Informed Consent/Demographics | L | -- | -- | -- | -- | -- | -- | -- | -- |
| Inclusion/Exclusion | L | -- | -- | -- | -- | -- | -- | -- | -- |
| Pre Dose Vitals/Urine Preg | L | L | -- | -- | L | -- | -- | L | L |
| Physical Examination | L | -- | -- | -- | -- | -- | -- | -- | L |
| Medical History | L | -- | -- | -- | -- | -- | -- | -- | -- |
| Laboratory Collection | L | -- | -- | -- | L | -- | -- | -- | L |
| Chest X Ray | -- | -- | -- | -- | -- | -- | -- | -- | -- |
| 6MWT/Borg Dyspnea Score | L | L | -- | -- | L | -- | -- | L | L |
| Post Dose Vital Signs | L | L | -- | -- | L | -- | -- | L | L |
| Signs and Symptoms of PAH | L | -- | -- | -- | L | -- | -- | -- | L |
| Lung Functions | L | -- | -- | -- | -- | -- | -- | -- | L |
| NYHA Functional Assessment | L | -- | -- | -- | L | -- | -- | -- | L |
| MLWHF Questionnaire | -- | -- | -- | -- | L | -- | -- | -- | L |
| Study Medication Dispensed/Returned | -- | L | L | -- | -- | -- | -- | -- | -- |
| Study Termination | -- | -- | -- | -- | -- | -- | -- | -- | L |
| Telephone Call | -- | -- | L | L | -- | L | L | -- | -- |
| Open Label Consent | -- | -- | -- | -- | -- | -- | -- | -- | -- |
| Open Label Eligibility | -- | -- | -- | -- | -- | -- | -- | -- | -- |
| Open Label Pre Dose Vital Signs | -- | -- | -- | -- | -- | -- | -- | -- | -- |
| Open Label Study Med | -- | -- | -- | -- | -- | -- | -- | -- | -- |

| Study Summary | Open Label Consent | | | | | | | | | | | | | | |
|---|---|---|---|---|---|---|---|---|---|---|---|---|---|---|---|
| | Open Label Eligibility | | | | | | | | | | | | | | |
| Safety | Open Label Pre Dose Vital Signs | L | L | L | L | L | L | L | L | L | L | L | L | L | C |
| | Open Label Study Med | L | L | L | L | L | L | L | L | L | L | L | L | L | C |
| Monitoring | Open Label Post Dose Vital Signs | L | L | L | L | L | L | L | L | L | L | L | L | L | C |
| Data Management | Open Label Lab Collection | L | L | L | L | L | L | L | L | L | L | L | L | L | C |
| Administration | Open Label Study Termination | L | L | L | L | L | L | L | L | L | L | L | L | L | C |

Study Documents

| L | Locked | C | Completed | I | Incompleted/Pending |
|---|---|---|---|---|---|
| Q | Queried | | Not Done | -- | Not Required |

Log Off

Visit Queries    (0 Visit Queries)

Adverse Events -- Total: 22   Coded: 22

| AE Name | From | To | Coded Name |
|---|---|---|---|
| INTERMITTENT SORE THROAT | 9-Jul-05 | 14-Aug-05 | Sore throat |
| DIARRHEA | 2-Mar-06 | 7-Dec-06 | Diarrhea |
| VOMITING | 2-Mar-06 | 7-Dec-06 | Vomiting |
| UPPER RESPIRATOY INFECTION | 14-Mar-06 | 28-Mar-06 | Upper respiratory infection |
| INCREASED RIGHT SHOULDER PAIN | 13-Jan-06 | 10-Nov-06 | Shoulder pain |
| HYPERCHOLESTEROLEMIA | UK APR 2006 | -- -- -- | Hypercholesterolemia |
| LEFT ARM PAIN | 26-Jul-06 | 19-Dec-06 | Pain in arm |

Figure 23D

| | | | | |
|---|---|---|---|---|
| RIGHT LOWER JAW TOOTHACHE | 23-Oct-06 | 25-Nov-06 | Toothache |
| LEFT LOWER JAW PAIN | 23-Oct-06 | 25-Nov-06 | Jaw pain |
| BLE EDEMA | 1-Nov-06 | --- | Edema of extremities |
| WORSENING COUGH | 1-Dec-06 | UK JAN 2007 | Cough aggravated |
| INTERMITTENT COUGH | 30-Jun-05 | 30-Jun-05 | Cough |
| WORSENING WHEEZING | 1-Dec-06 | UK JAN 2007 | Wheeze worsened |
| SINUS INFECTION | 2-Jan-07 | UK FEB 2007 | Sinus infection |
| CHEST COLD | 25-Sep-07 | 10-Oct-07 | Chest cold |
| INTERMITTENT HEADACHES | 9-Jul-05 | 18-Jul-05 | Intermittent headache |
| INTERMITTENT HEADACHES | 5-Aug-05 | 10-Nov-06 | Intermittent headache |
| INTERMITTENT JAW PAIN | 27-Jul-05 | 1-Sep-05 | Jaw pain |
| INTERMITTENT COUGH | 27-Jul-05 | --- | Cough |
| TOOTH EXTRACTION | 29-Aug-05 | 29-Aug-05 | Tooth extraction |
| WHEEZING | 5-Sep-05 | UK JUN 2007 | Wheezing |
| SORETHROAT | 2-Mar-06 | 10-Nov-06 | Sore throat |

Concomitant Medications and Therapies -- Total: 38  Coded: 38

| Verbatim | Indication | From | To | ATC Code | ATC Text | WHO DRUG TEXT |
|---|---|---|---|---|---|---|
| TRACLEER | PULMONARY ARTERIAL HYPERTENSION | 12-Mar-02 | | C02KX | OTHER ANTIHYPERTEN SIVES | Tracleer |

Study Summary
Safety
Monitoring
Data Management
Administration
Study Documents
Log Off

Figure 23E

| | | | | |
|---|---|---|---|---|
| DIOVAN | HYPERTENSION | UK UKN 2000 | | C09CA | Angiotensin II antagonists, plain | Diovan |
| TIAZAC | HYPERTENSION | UK UKN 1995 | | C08DB | Benzothiazepine derivatives | Tiazac |
| COUMADIN | PULMONARY ARTERIAL HYPERTENSION | UK NOV 2000 | 8-Aug-05 | B01AA | Vitamin K antagonists | Coumadin |
| LASIX | RIGHT SIDED HEART FAILURE | UK UKN 1996 | 29-May-06 | C03CA | Sulfonamides, plain | Lasix |
| ALLOPURINOL | GOUT | UK UKN 1990 | | M04AA | Preparations inhibiting uric acid production | Allopurinol |
| PROPOXYPHENE | GENERALIZED JOINT PAIN | UK UKN 2001 | | N02AC | DIPHENYLPROPYLAMINE DERIVATIVES | Propoxyphene |
| TRICOR | HYPERCHOLESTEROLEMIA | UK UKN 2004 | | C10AB | FIBRATES | Tricor |
| OXYGEN | PULMONARY ARTERIAL HYPERTENSION | UK SEP 2000 | | V03AN | MEDICAL GASES | Oxygen |
| AMOXICILLIN | DENTAL PROPHYLAXIS | 27-Aug-05 | 28-Aug-05 | J01CA | Penicillins with extended spectrum | Amoxicillin |

Study Summary
Safety
Monitoring
Data Management
Administration
Study Documents
Log Off

Figure 23F

| | | | | | | |
|---|---|---|---|---|---|---|
| CARBOCAINE 3 | TOOTH EXTRACTION | 29-Aug-05 | 29-Aug-05 | N01BB | AMIDES | Carbocaine |
| MEPIVACAINE HYDROCHLORIDE | TOOTH EXTRACTION | 29-Aug-05 | 29-Aug-05 | N01BB | Amides | Mepivacaine hydrochloride |
| COUMADIN | PAH TAKES 14MG EVERY DAY EXCEPT TUESDAYS TAKES 16MG | 9-Aug-05 | 29-Aug-05 | B01AA | Vitamin K antagonists | Coumadin |
| COUMADIN | PAH | 30-Aug-05 | 13-Jul-06 | B01AA | Vitamin K antagonists | Coumadin |
| METHYLPREDNISOL ONE | INCREASED RIGHT SHOULDER PAIN | 24-Jan-06 | 24-Jan-06 | H02AB | Glucocorticoids | Methylprednis olone |
| ADVAIR DISKUS | WHEEZING | 13-Apr-06 | UK MAY 2007 | R03AK | ADRENERGICS AND OTH.DRUGS FOR OBSTRUCT.AIR WAY DIS. | Advair |
| CRESTOR | HYPERCHOLESTE ROLEMIA | 13-Apr-06 | | C10AA | HMG CoA reductase inhibitors | Crestor |

Study Summary
Safety
Monitoring
Data Management
Administration
Study Documents
Log Off

Figure 23G

| | | | | | |
|---|---|---|---|---|---|
| PROMETHAZINECO DEINE SYRUP | UPPER RESPIRATORY INFECTION | 14-Mar-06 | 14-Apr-06 | R05DA | Opium alkaloids and derivatives | Promethazine w/codeine |
| DIPHENOXYLATE ATROPINE | DIARRHEA | 14-Mar-06 | 14-Apr-06 | A07DA | Antipropulsives | Diphenoxylate w/atropine sulfate |
| PROMETHAZINE | NAUSEA | 14-Mar-06 | 14-Apr-06 | N05C | HYPNOTICS AND SEDATIVES | Promethazine |
| LASIX | RIGHT SIDED HEARTFAILURE | 30-May-06 | 29-Jan-07 | C03CA | Sulfonamides, plain | Lasix |
| COUMADIN | PAH | 14-Jul-06 | 1-Oct-06 | B01AA | Vitamin K antagonists | Coumadin |
| PENICILLIN VK | TOOTHACHE | 23-Oct-06 | 23-Nov-06 | J01CE | Beta-lactamase sensitive penicillins | Penicillin vk |
| HYDRALAZINE | HYPERTENSION | 21-Nov-06 | | C02DB | Hydrazinophthalazine derivatives | Hydralazine |
| ZITHROMAX | UPPER RESPIRATORY INFECTION | 19-Dec-06 | 24-Dec-06 | J01FA | Macrolides | Zithromax |
| XOPENEX INH | WHEEZING | 2-Jan-07 | 15-Jun-07 | R03AC | Selective beta-2-adrenoreceptor agonists | Xopenex |

Study Summary
Safety
Monitoring
Data Management
Administration
Study Documents
Log Off

Figure 25

| | | Product Presentation Reportal - Windows Internet Explorer | |
|---|---|---|---|

CRF: Laboratory Collection
Subject: 10001
Initial: ELG
Birthday: 31 JUL 1953
Visit: WEEK 12 VISIT 5
Visit Date: 09/12/2005
Completed: Feb 13 2006 2:59PM What is the status of the labs analyzed at the site?        1

☑ Done (Collected)
☐ Not Done (Not Collected)

[Generate Query]  Query History | Audit History

Enter the date the samples were collected
Date:

Month        Day        Year
[SEP]        [20]       [2005]

[Generate Query]  Query History | Audit History

| Test Group: Hematology (CBC) | Results | | Clinically Significant (CS) Not Clinically Significant | Not Resolved |
|---|---|---|---|---|
| *Check if hematology sample not noted* | | | | |
| WBC | 3.8 | x10.2 ml | ○ CS ◉ NCS | ☐ |
| RBC | 5.9 | x10.6 ml | ○ CS ◉ NCS | ☐ |
| Hemoglobin | 16.6 | g/dl | ○ CS ◉ NCS | ☐ | ately located at doctors' offices, hospitals or clinics, depending upon the therapeutic area of the study itself. Each Site will recruit and enroll patients into the study until the number of patients required for the appropriate statistical analyses has been reached. The larger the study and the more countries involved, the more staff will be required. The number of Sites and CROs required to conduct the study may also be larger.

AUTOMATED IDENTIFICATION OF TASKS THAT MUST BE COMPLETED BEFORE A CLINICAL TRIAL DATABASE CAN BE LOCKED

CROSS-REFERENCE TO RELATED APPLICATIONS

This application claims the benefit of U.S. Provisional Patent Application No. 61/091,142 filed Aug. 22, 2008.

COPYRIGHT NOTICE AND AUTHORIZATION

Portions of the documentation in this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

Pharmaceutical, Biotechnology, Bio-Pharmaceutical, Medical Device Companies and academic researchers conduct clinical studies to evaluate the safety and efficacy of new products to help determine suitability for the market. These groups or companies are known as Clinical Trial Sponsors. An important part of the clinical study is to collect a variety of clinical data on patients to test the product in a controlled setting. These data are typically presented by the Sponsor in a variety of formats including various statistical analyses to the appropriate regulatory agencies, such as the Food and Drug Administration for review and approval.

A clinical study team can be comprised of many individuals, from many organizations, and from many countries. In addition to the Sponsor, there is usually a group, or groups, tasked with conducting the study on behalf of the Sponsor. These groups are known as Clinical Research Organizations (CROs). In addition to the Sponsor and CROs, the study employs Clinical Sites (Site) which are managed by physicians, known as the Principal Investigator (PI). Sites are typically located at doctors' offices, hospitals or clinics, depending upon the therapeutic area of the study itself. Each Site will recruit and enroll patients into the study until the number of patients required for the appropriate statistical analyses has been reached. The larger the study and the more countries involved, the more staff will be required. The number of Sites and CROs required to conduct the study may also be larger.

The integrity of the data collected in the study is paramount to the success of the study. The staff of the Sites, as defined by the Sponsor, must carefully execute the clinical protocol. All data must be properly recorded in compliance with Good Clinical Practice (GCP) policy, as well as other local and global regulations for study conduct. In order to ensure data integrity and regulatory compliance, personnel are dispatched to the Sites to review clinical data, protocol compliance, and regulatory compliance. These personnel are known as Study Monitors (Monitors) or Clinical Research Associates (CRA). Any monitor can make several trips to their Site during the course of the study. During each visit, the monitor checks various electronically entered clinical data against their source sheets for accuracy. The monitor can then either accept the Case Report Form (CRF) if there have been no discovered discrepancies, or create a query where an inconsistency occurs. The time that monitors spend at a site is very limited. Thus, having a focused plan of action to review outstanding data issues saves valuable time. Monitors often have no way to know what data-related issues may exist, and must perform quite a bit of discovery once they arrive at the site.

Locking a clinical database is essentially freezing all entry or changes to data once the data has been reviewed and accepted by the clinical team working on the study. This can be a laborious and time-consuming process that can have many stages of lock. Soft lock of a database typically includes a subset of the overall database made up of the key efficacy and safety data points. A hard lock typically includes all of the data points in the database. An interim lock includes a subset of the database up to a certain number of patients reaching a certain time point in the study. There are many steps in the lock process that can delay the process of collecting, cleaning and verifying the accuracy of the data. These include data entry into the CRF, having the CRF signed by the site personnel, having the CRF data reviewed by the CRA for accuracy, the CRA locking the CRF, and coding the data into standard dictionaries. The traditional process for these activities takes a significant amount of time, since tracking the status of each activity as it occurs is a major challenge.

The impact on patient heath is also compromised by product approval delays. Such result in important treatments not yet being available to patients who need them. The business impact on these delays is also significant. The longer it takes to complete the analysis of the study data, the longer it takes to get the product to market. Each month of delay could cost the sponsor hundreds of millions of dollars in revenue at the time the product is at peak sales on the market.

Accordingly, there is an unmet need for methods and systems that can speed up the database locking process. The present invention fulfills such a need.

BRIEF SUMMARY OF THE INVENTION

One preferred embodiment provides an automated method of managing a database lock for a clinical trial study. The clinical trial study is managed using a database that includes clinical trial data and the status of the data for a plurality of patients. The method operates as follows:

1. A lock criteria is defined for the study.

2. A processor is used to automatically generate a list of tasks that must occur to achieve the lock using the clinical trial data and the status of the data.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIGS. 5-25 show user interface display screens in accordance with one embodiment of the present invention.

DETAILED DESCRIPTION OF THE INVENTION

Figure 1:
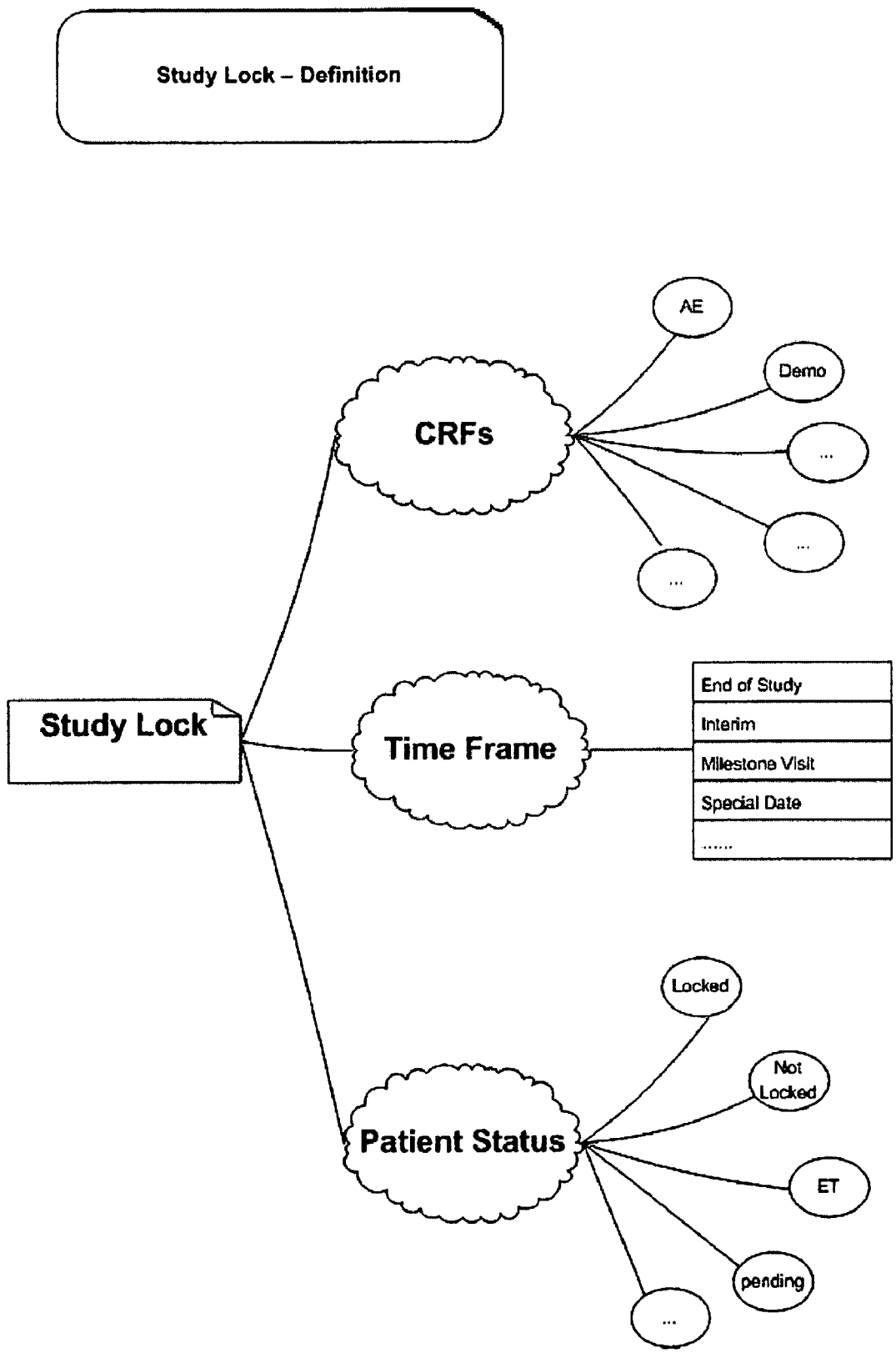
FIGS. 1-3 show objects used in one accordance with one preferred embodiment of the present invention.

Certain terminology is used herein for convenience only and is not to be taken as a limitation on the present invention.

This patent application includes an Appendix having a file named appendix.txt, created on Aug. 22, 2008, and having a size of 48,955 bytes. The Appendix is incorporated by reference into the present patent application. One preferred embodiment of the present invention is implemented via the source code in the Appendix. The Appendix is subject to the "Copyright Notice and Authorization" stated above.

The present invention is described in the context of a web-based service. However, the scope of the present invention is not limited to this particular implementation of the invention. The present invention is described in the context of a plurality of distributed computers, all of which are linked together by an electronic network, such as a LAN or the Internet. The computers may be any type of computing device that allows a user to interact with a web site via a web browser. For example, the computers may be personal computers (PC) that run a Microsoft Windows® operating system. The computers may also be handheld, wireless devices.

I

I. Overview of Present Invention

The system described herein provides a means to define the lock criteria for a database. In other words, one can define a subset of data in the overall database or the overall database itself as the target to be locked. The term "locked" means the data is locked from further editing by the study team, and has been determined to be "clean," meaning that the data has passed a series of review steps that include source verification monitoring by the CRA at the clinical sites, programmatic verification by clinical data managers, and medical verification by physicians. In most cases, the database must be formally locked before the study data can be formally analyzed by biostatisticians, and approvals from the above groups are required prior to lock. Once locked, the data may be "unblinded" for analysis. Unblinding provides the study team access to blinded treatment codes which identify the specific treatments provided to each patient. For example, some patients are taking placebo while other may be taking various doses of active treatment. These treatments are kept blinded to prevent a bias in treatment or subjective evaluations by the site doctors, study team or patients themselves.

The lock criteria for a complete study in most cases will include the entire database. There are many instances where a database lock may include a subset of the data. These are known in the industry as "interim locks" or "soft locks." Interim locks typically are done prior to an interim analysis, and are also built into the overall study design. The concept is to look at both the efficacy and safety of a drug or device prior to the completion of the study. An interim lock may be defined by many variables. These include some number of patients that have completed some number of study visits. For example, a study may be designed to treat 100 patients for six monthly treatment visits. An interim analysis may be defined to look at data for the first 50 patients to complete five months of treatment. Once these variables are put into the system, specific reports may be generated regarding which patients will be included in the lock, and which data for those patients are to be included in the lock. Additional reports display all tasks required to clean the data to achieve the lock.

Another type of lock definition is a soft lock. A soft lock typically includes only the key primary efficacy and safety values for all patients. The full database lock, or a hard lock, will include all variables for all patients. There can be as many definitions for lock criteria as there are designs for clinical studies. Some can be very straightforward and some quite complex. In some study designs, patients are offered the opportunity to participate in an "open label extension." This allows patients who may have been treated with a placebo, a comparator or lower doses of an active compound or treatment to all take the preferred dose of the active compound or treatment for a number of months or years after the blinded study has been completed. This is increasingly done to collect more safety data on patients up until the point where the product is approved for market by a regulatory agency such as the FDA. Accordingly, a hard lock could include all of the blinded study data as well as any available open label data, up to a specific point in time. This further complicates the task of the study team in cleaning the data and focusing their efforts exclusively on the data to be included in the lock. This can be quite a daunting task, especially in large studies with a tight deadline to lock the data.

A database lock can be accomplished more rapidly by identifying the remaining tasks for a specific lock, and focusing the attention of the monitors and data managers on those specific tasks. Examples of such tasks are as follows:

1. Monitoring and locking activities—monitors may lock a specific CRF after review provided there are no queries pending.

2. Identification of missing or incomplete CRFs.

3. Identification of CRFs that remain unsigned by the physician.

4. Identification of items such and medications and adverse events that need to be coded to a standard dictionary.

5. Summarize the status of reaching database lock

6. Provide detailed task lists to the monitors for remaining tasks

Preferred embodiments of the present invention use a computer-based electronic system for collecting, reviewing, and querying clinical case report forms (CRFs.) In addition, the system displays the management status of each CRF and summarizes the required actions on a monitor-by-monitor, site-by-site, and patient-by-patient basis for a successful database lock. In effect, the system notifies each monitor of the exact tasks that remain at a given site so they may focus their efforts on those specific tasks. The study team managers may view summaries of the status for each monitor to more effectively direct the work activities of the monitors. The system uses programming objects to present report screens to users via a web browser interface. System users are provided role-based access to perform the monitoring tasks and generate the reports. The data and reports are stored in a database though a web-based interface using a series of processing objects. Additional processing objects could be added to perform additional functions. An administrative user can create the access identity for other system users as follows:

| User Type | Type of Access |
| --- | --- |
| Sponsor | Views reports and summary data for all sites |
| Project Manager | Views reports and summary data for all sites |
| Monitor | Views reports and summary data for their specific region(s) |
| | Views task lists for their sites |
| Administrator | Manage user access |
| | Defines lock criteria |

A prerequisite for using the system is to have the system configured with correct case report forms (CRFs) to reflect the requirements of the study protocol. Next is to deploy data collection tools to the clinical sites for data entry. Sites will then be able to record clinical data which will be aggregated into the central clinical database.

Once the clinical database is ready to collect clinical data, the process works as follows:

1. Database lock criteria are defined and entered into the system by an administrative user. The system generates a summary list of the status of all clinical sites and tabulates metrics for each site that are defined in a "site object," based on the lock criteria of the study defined in a "study lock object." The system generates a summary list of the status of each patient within a clinical site and tabulates metrics for each patient that are defined in a "patient object," based on the lock criteria of the study defined in the study lock object.

2. Finally, the system creates a task list for a given site based on open items for each patient as compared to the lock criteria in the study lock object. The details of the objects are described below.

Figure 3:
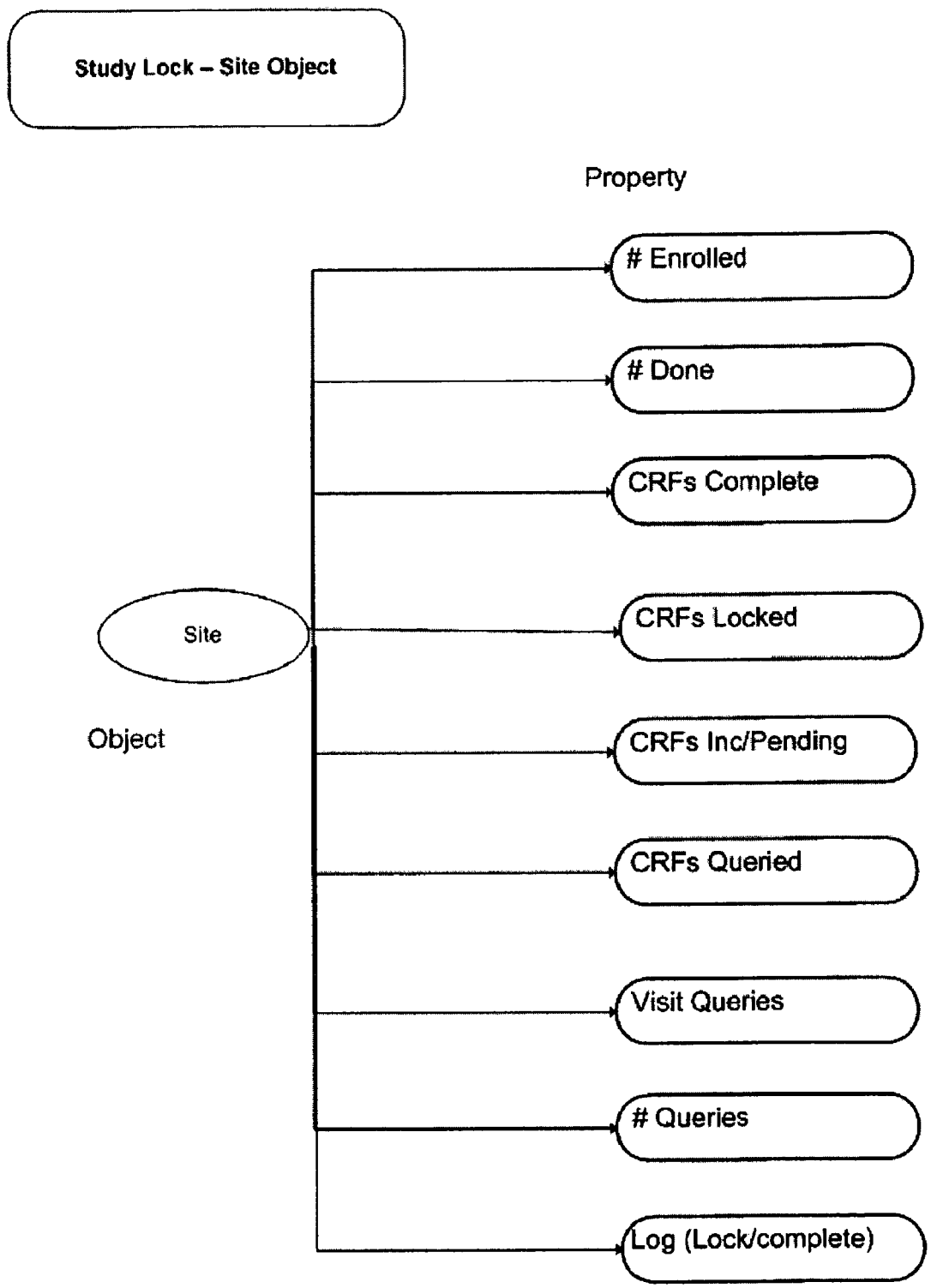

Objects:

A "Site Object" has 9 Properties, as Follows (See FIG. 3):

| | |
|---|---|
| # Enrolled | total enrolled patients |
| # Done | number of locked patients |
| CRFs Complete | number of complete CRFs |
| CRFs Locked | number of locked CRFs |
| CRFs Inc/Pending | number of incomplete or pending CRFs |
| CRFs Queried | number of CRFs with open queries |
| Log (Lock/Complete) | number of locked and complete Log CRFs (Adverse Events (AE), (Concomitant Meds (ConMeds), etc.) |
| Visit Queries | number of open queries on visit date |
| # Queries | number of open queries |

Figure 2:
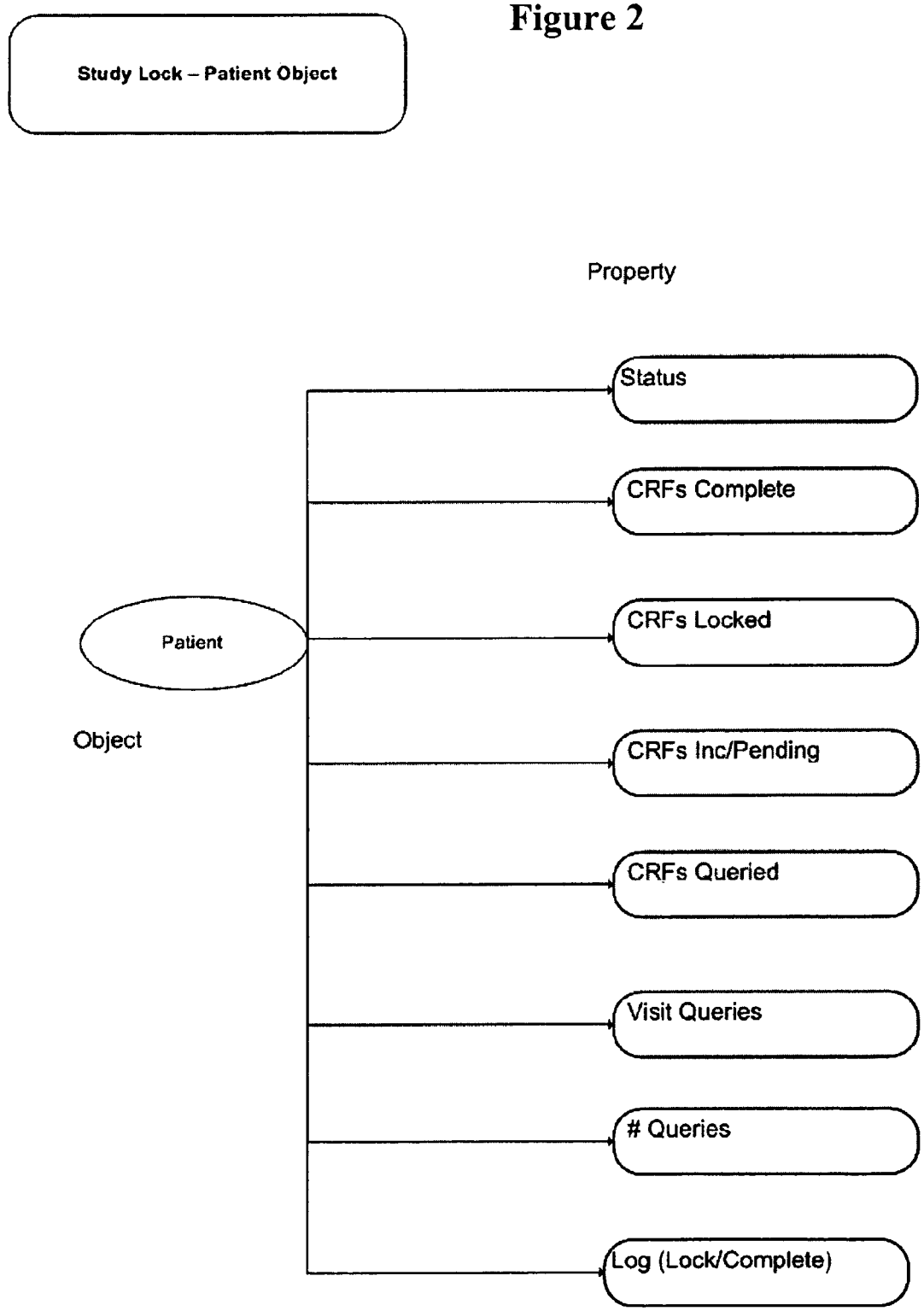

A "Patient Object" has 8 Properties (See FIG. 2):

| | |
|---|---|
| Status | patient status: locked or not; complete, discontinued or pending |
| CRFs Complete | number of complete CRFs |
| CRFs Locked | number of locked CRFs |
| CRFs Inc/Pending | number of incomplete or pending CRFs |
| CRFs Queried | number of CRFs with open queries |
| Visit Queries | number of open queries on visit date |
| Log (Lock/Complete) | number of locked and complete Log CRFs (AE, ConMeds etc) |
| # Queries | number of open queries |

A "Study Lock Object" has 3 Properties (See FIG. 1):

| | |
|---|---|
| CRFs List | list of the CRFs to the used in the lock |
| Timeframe | list of the time points to be used in the lock |
| Status | list of the categories of patients to be used in the lock |

Types of Reports:

1. Lock Summary

A brief view of all Site objects based on chosen country and site options. This report also give a total number of all selected sites.

2. Lock Site Detail

A brief view of all Patient objects of a given site. If user wants to learn what tasks are left to make a patient locked, the user can get more detailed information from a Remaining Task List report.

3. Remaining Task List

Listing of all tasks left for a given site to make patient(s) become locked.

4. Lock Patient Detail

Provides the subset of CRF data view. A user can view all required CRFs here. Based on the requirement of the study, it will display some special CRFs datasets, such as Adverse/Serious Events, Concomitant Medications, and Therapies.

II. Detailed Disclosure

Figure 4:
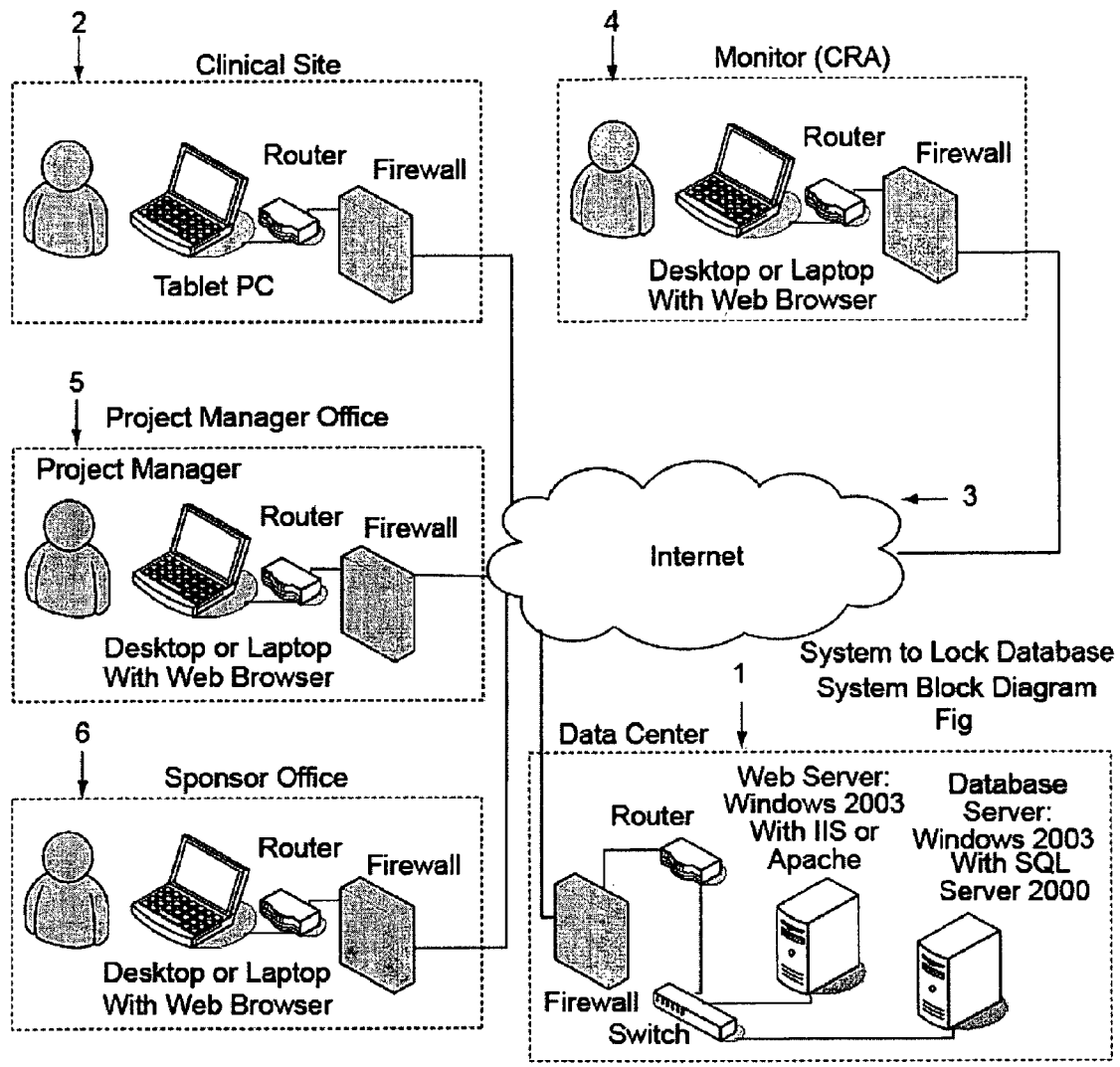
FIG. 4 shows a schematic diagram of a hardware configuration in accordance with one preferred embodiment of the present invention.

The initial system configuration is put together as shown in FIG. 4. Item 1 depicts the central data center where the database is stored and the system processes the reports. Clinical Data is entered at the clinical site (item 2) and transmitted through the internet (item 3) to the data center (item 1). A clinical monitor can view the data, lock specific CRFs, create clinical queries, and acknowledge responses to queries on a remote computer (item 4) or at the clinical site (item 2.) The clinical project manager who directs the activities of the monitors, may do so from the computer at their office (item 5). The sponsor of the study may view the overall progress of the data lock from a computer in their office (item 4).

A system administrator or data manager will enter the criteria for a lock into the system as shown in FIG. 5. The data for the criteria is stored in an object depicted in FIG. 1. First, the name of the lock criteria is defined (FIG. 5, item 1) and saved. Next, the subset of CRF types to be included in the criteria is selected from the available CRFs in the clinical database (FIG. 5, item 2). The time points, which are typically predetermined schedule assessment points defined by the clinical protocol, are then selected, or a specific date which include the selected visits completed up to a certain date is selected (FIG. 5 item 3.) Finally, the type of patients to include in the lock are selected (FIG. 5, item 4). Available patient types may vary depending upon the design of the study. Once the criteria have been selected, they are saved (FIG. 5, item 5) in the object shown in FIG. 1. Two examples of lock criteria are shown. The first example is called a "soft lock" which is a subset of CRFs up to a certain visit. An example of a summary report for a soft lock is shown in FIGS. 12a and 12b. A second example is called a "hard lock." In this case, the criteria include all CRFs up to a specific date as shown in FIG. 20.

Figure 6:
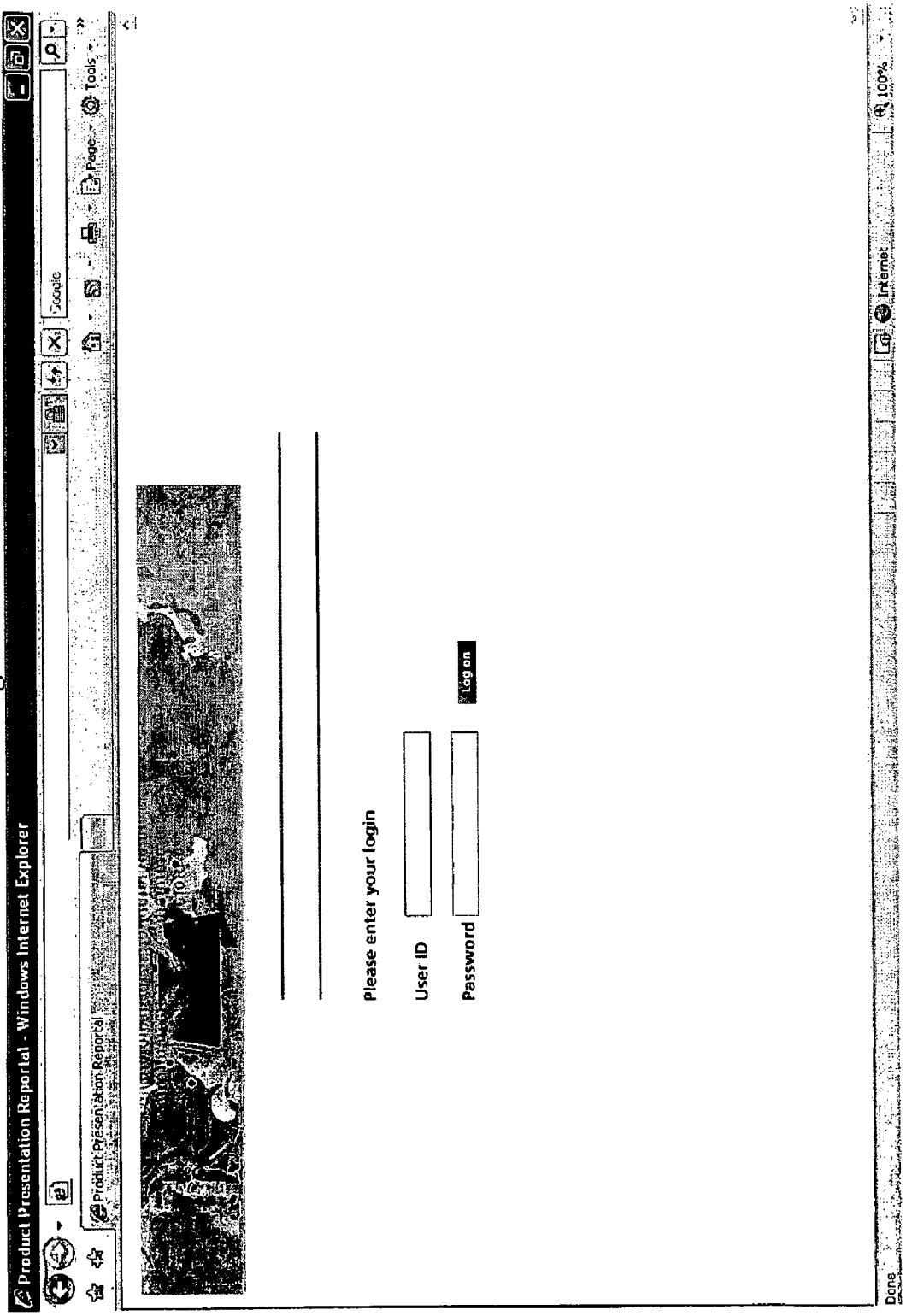
Figure 7:
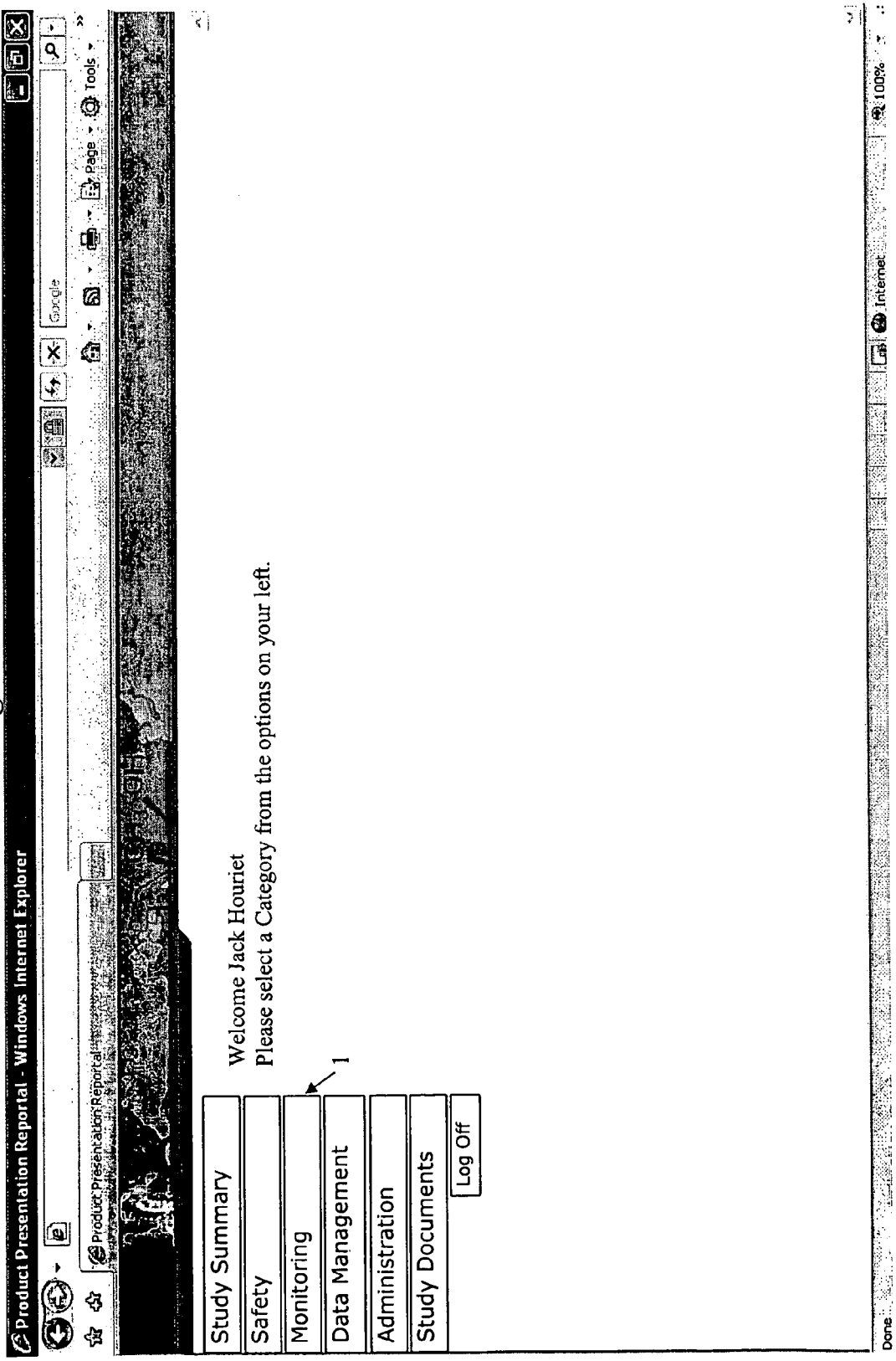
Figure 9:
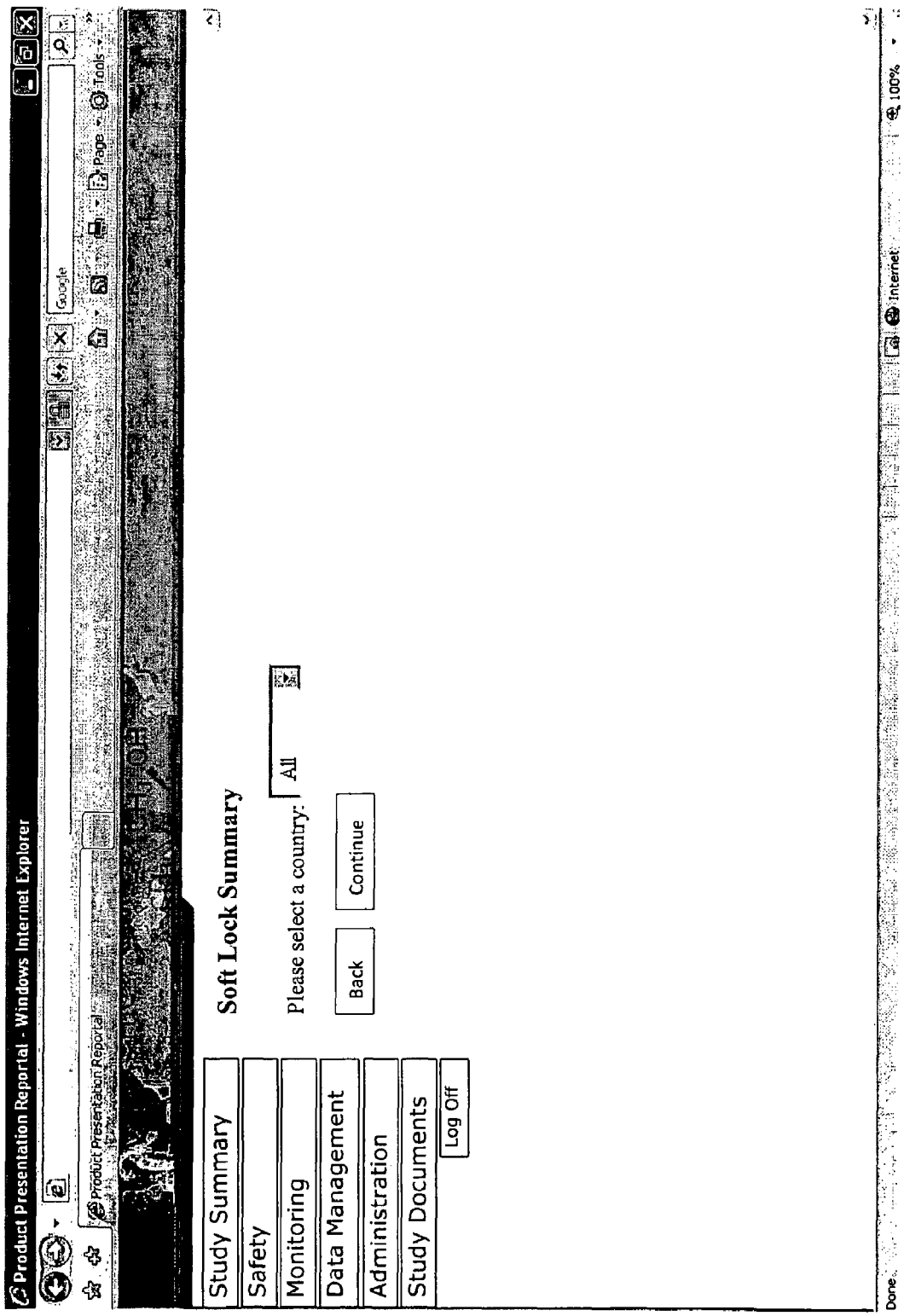
Figure 10:
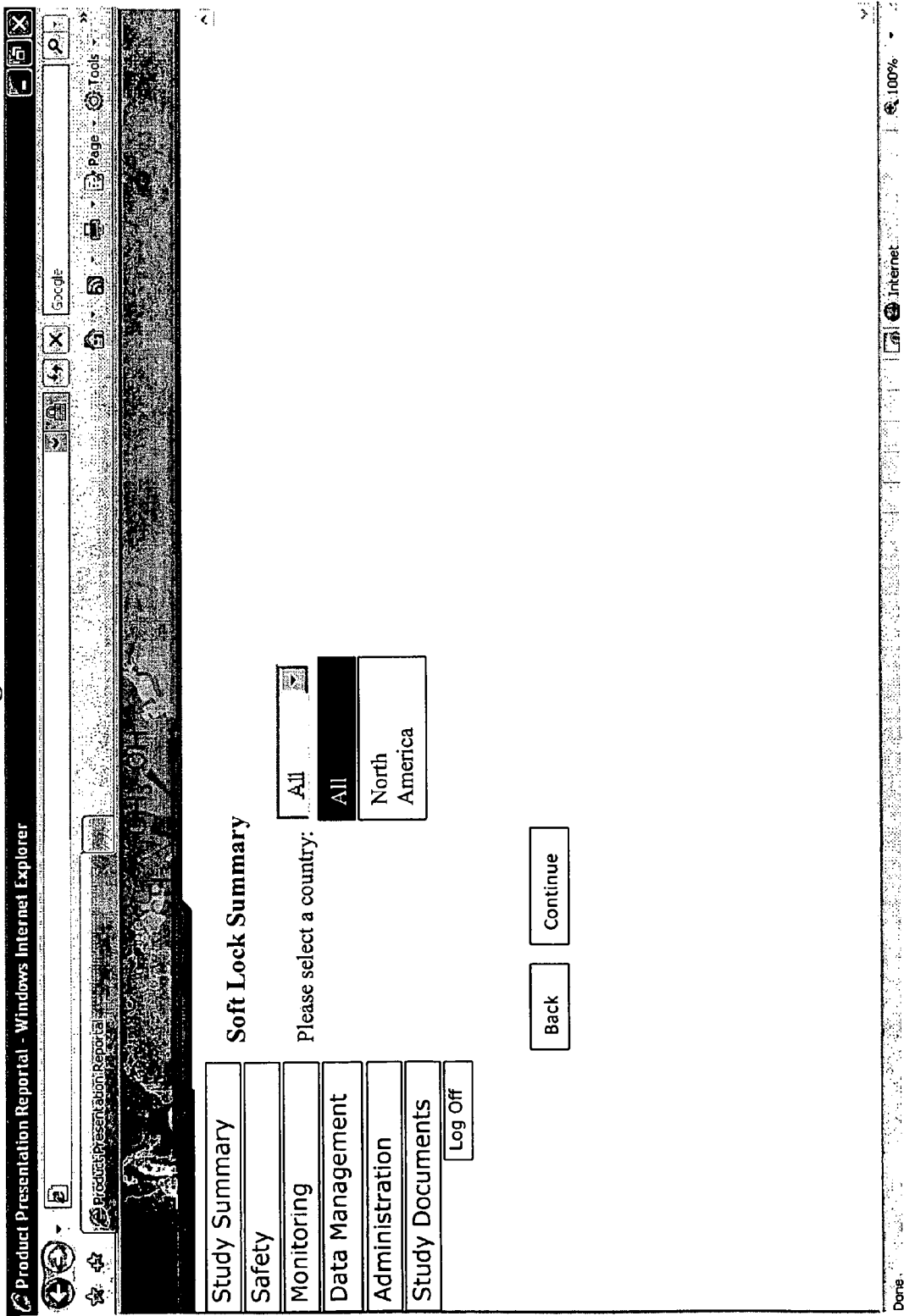
Figure 11:
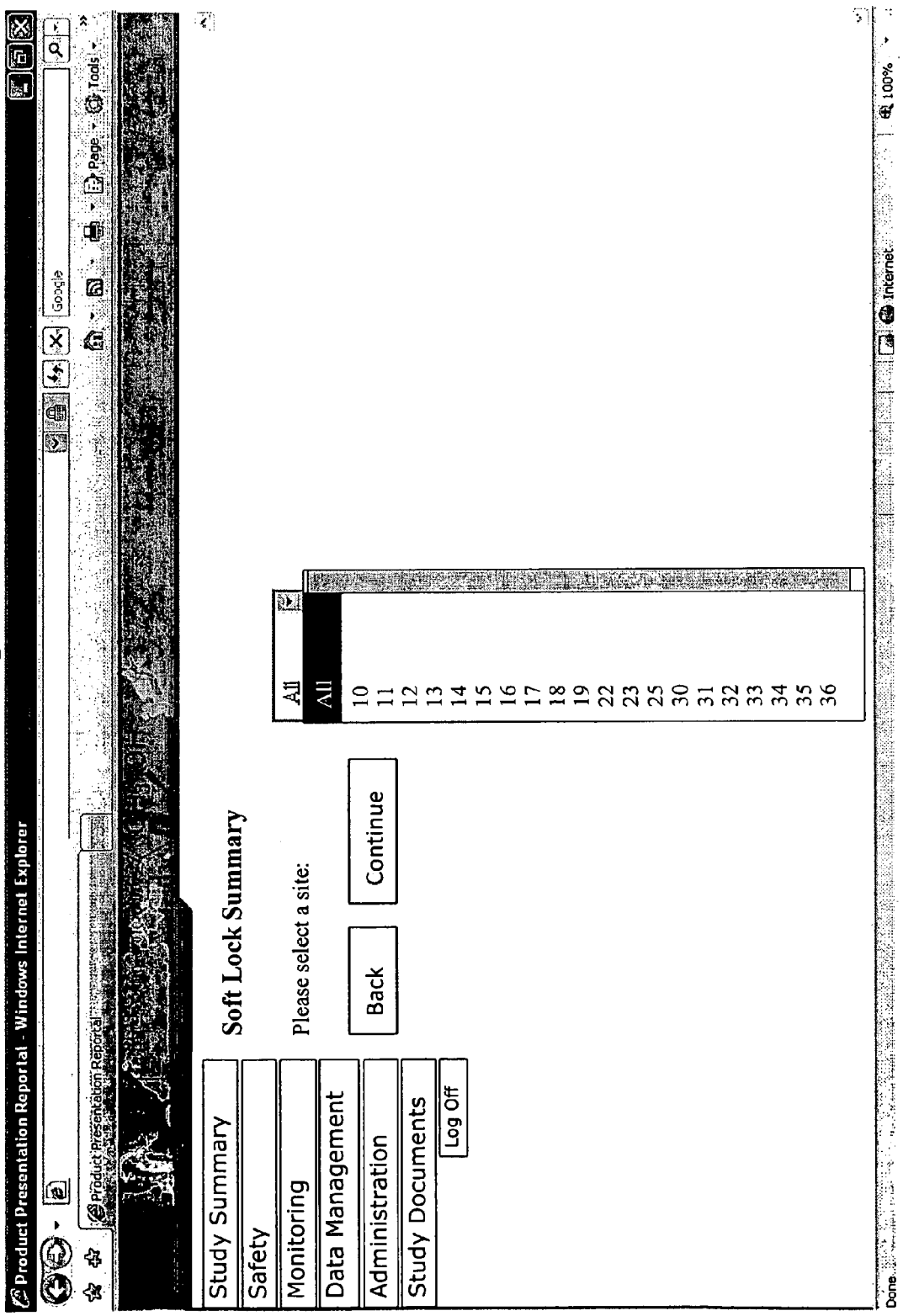

To view the summary report for the soft lock, a user logs into the system (FIG. 6). The user then selects the monitoring tab from the category list (FIG. 7, item 1). The user selects the Soft Lock Summary (FIG. 8, item 1), the geographic regions of the sites (FIGS. 9 and 10), and the range of clinical sites within that geography (FIG. 11). Upon completion of the selections, the report will appear (FIGS. 12a and 12b).

The summary report indicates the site number (FIG. 12a, item 1), the number of patients enrolled (FIG. 12a, item 2), and the number of patients who are clean having no outstanding tasks to be addressed (FIG. 12a, item 3). These patients are considered "done" having no further work required. The number of CRFs collected for that site is displayed (FIG. 12a, item 4) and the number of which have been locked is displayed (FIG. 12a, item 5). The number of CRFs requiring signature from a physician are displayed (FIG. 12a, item 6). Also displayed is a summary of the number of CRFs having open clinical queries (FIG. 12a, item 7), the number of queries related to a visit date (FIG. 12a, item 8), and the total number of outstanding clinical queries at the site (FIG. 12a, item 9).

A detail report for a given site can be created by selecting the hyperlink as shown in FIG. 12a, item 10. The site detail report shown in FIG. 13 contains the patient number (item 1), the patient status (item 2), CRFs completed and required (item 3), CRFs locked (item 4), CRFs incomplete or pending signature (item 5), the number of CRFs with clinical queries awaiting resolution (item 6), the number of visit date queries which applies to all the CRFs in a single visit (item 7), and the total number of queries for each patient (item 8).

Figure 14:
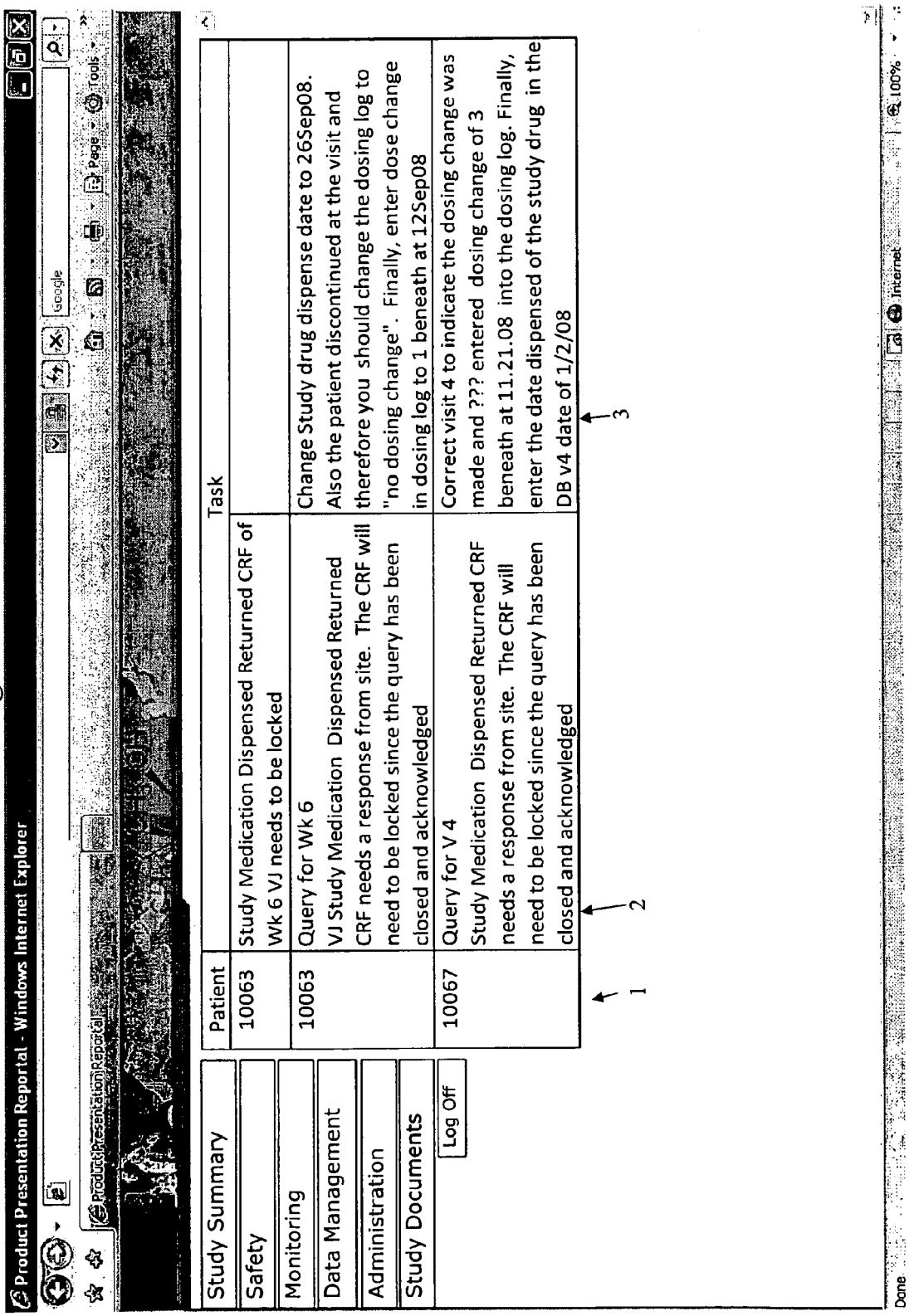

The task list for that site may be selected by clicking on the link in FIG. 13, item 9. The task list itself is shown in FIG. 14. It outlines the specific tasks required to have each patient clean and locked. The patient number is shown in item 1, and the specific task items are shown in item 2, and if a task has a clinical query pending, the details are shown in item 3.

The details of all of the CRFs needed for a specific patient (FIG. 15a) may be viewed by selecting the patient number link (FIG. 13, item 11). FIG. 15a, item 1 shows the grid of CRFs (item 2) and visits (item 3) specific to the lock criteria. FIG. 15b shows an example for another patient.

The purpose of these tools is to focus the monitoring activity done by the CRAs on the specific tasks required to meet the lock criteria, and not on tasks that can wait. This maximizes the efficiency of each monitoring visit at the clinical sites.

Figure 8:
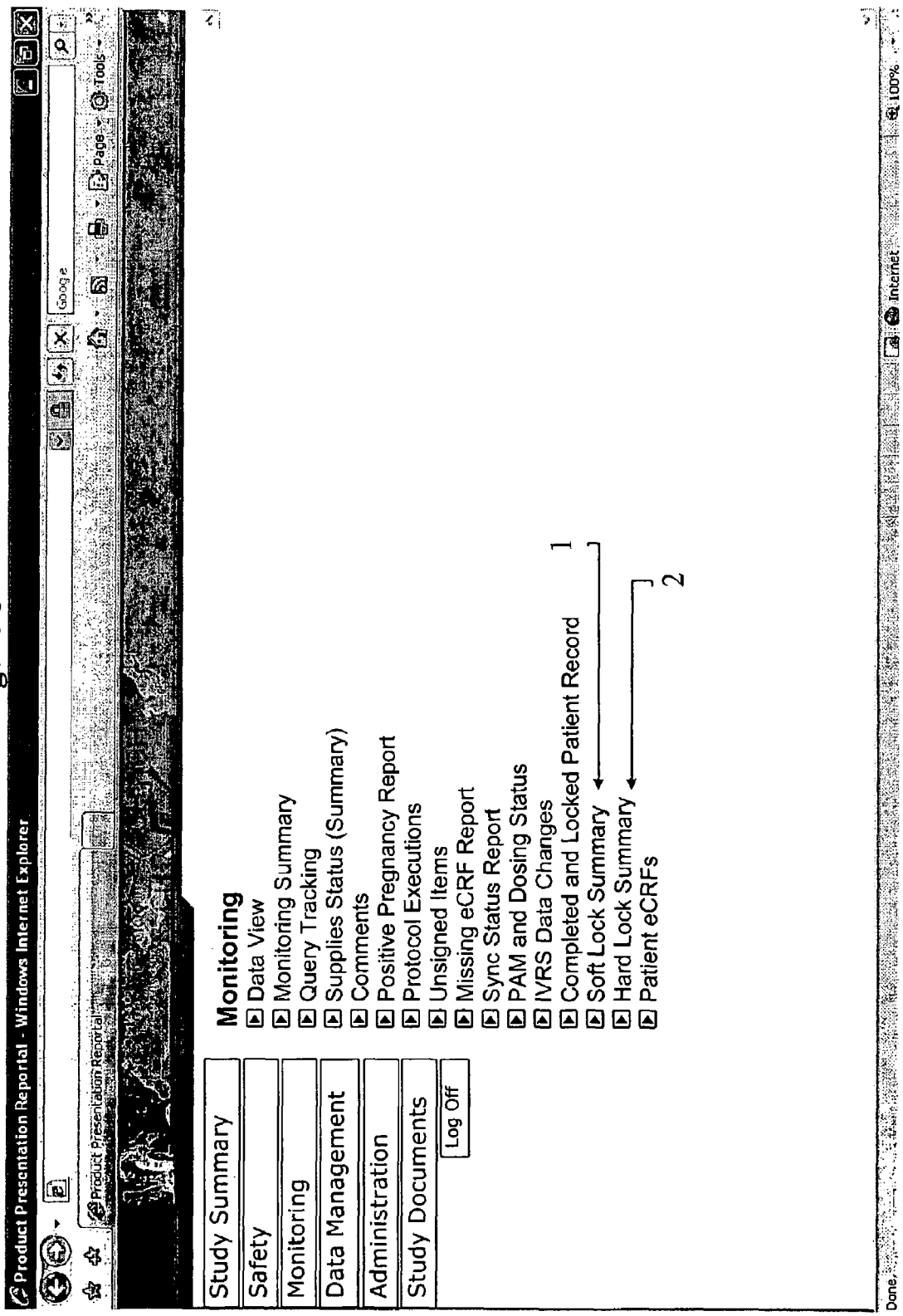
Figure 16:
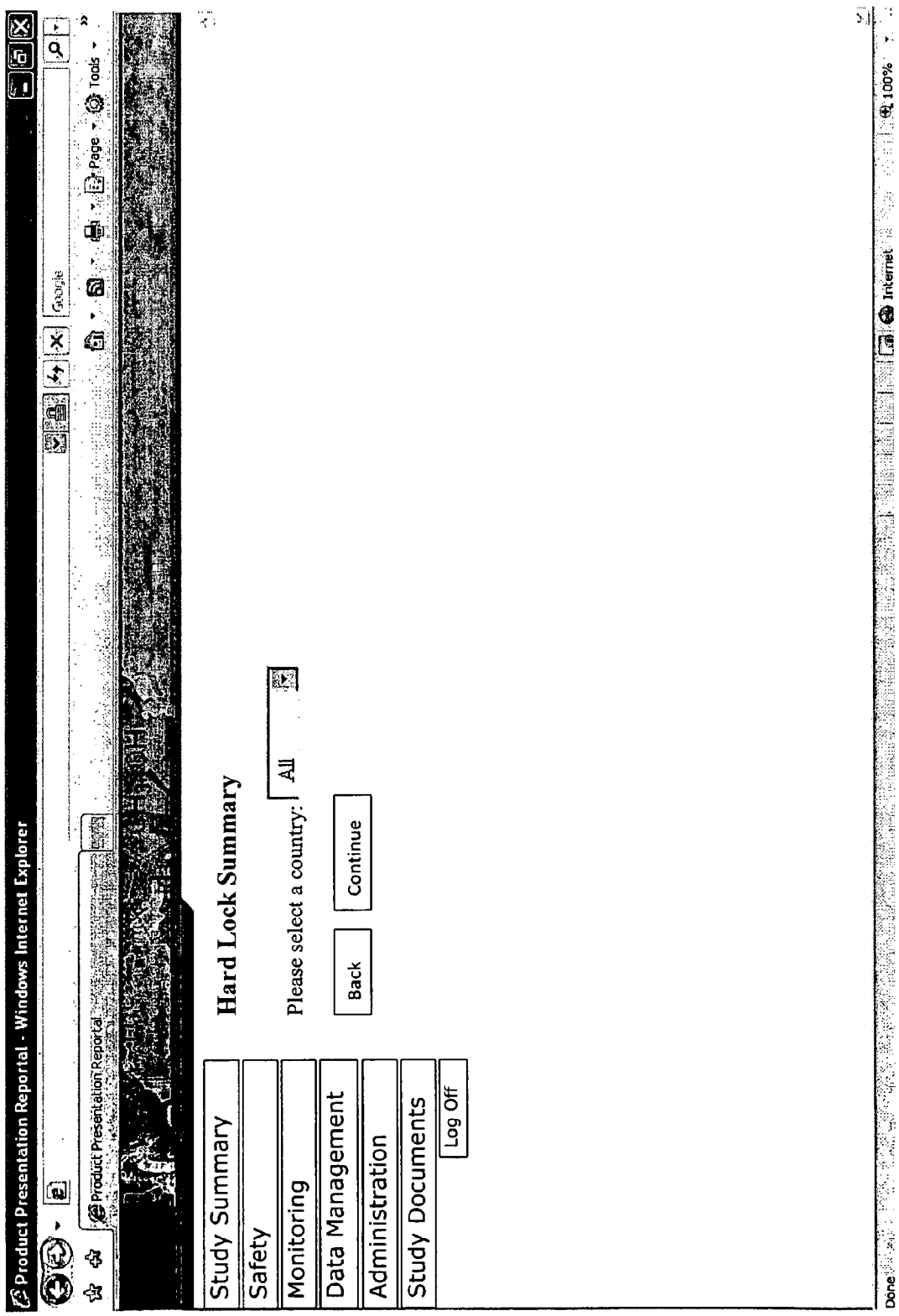
Figure 17:
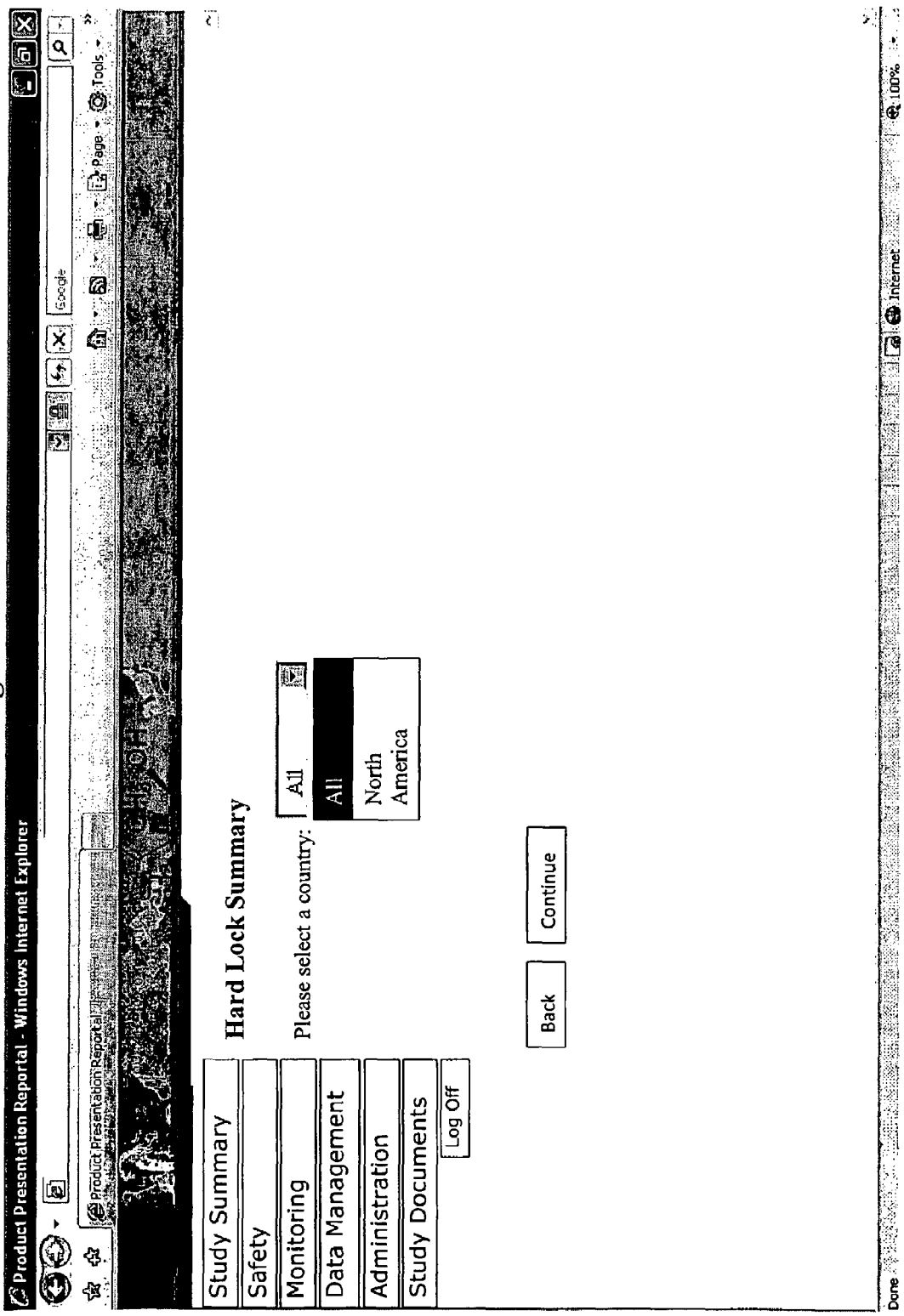
Figure 18:
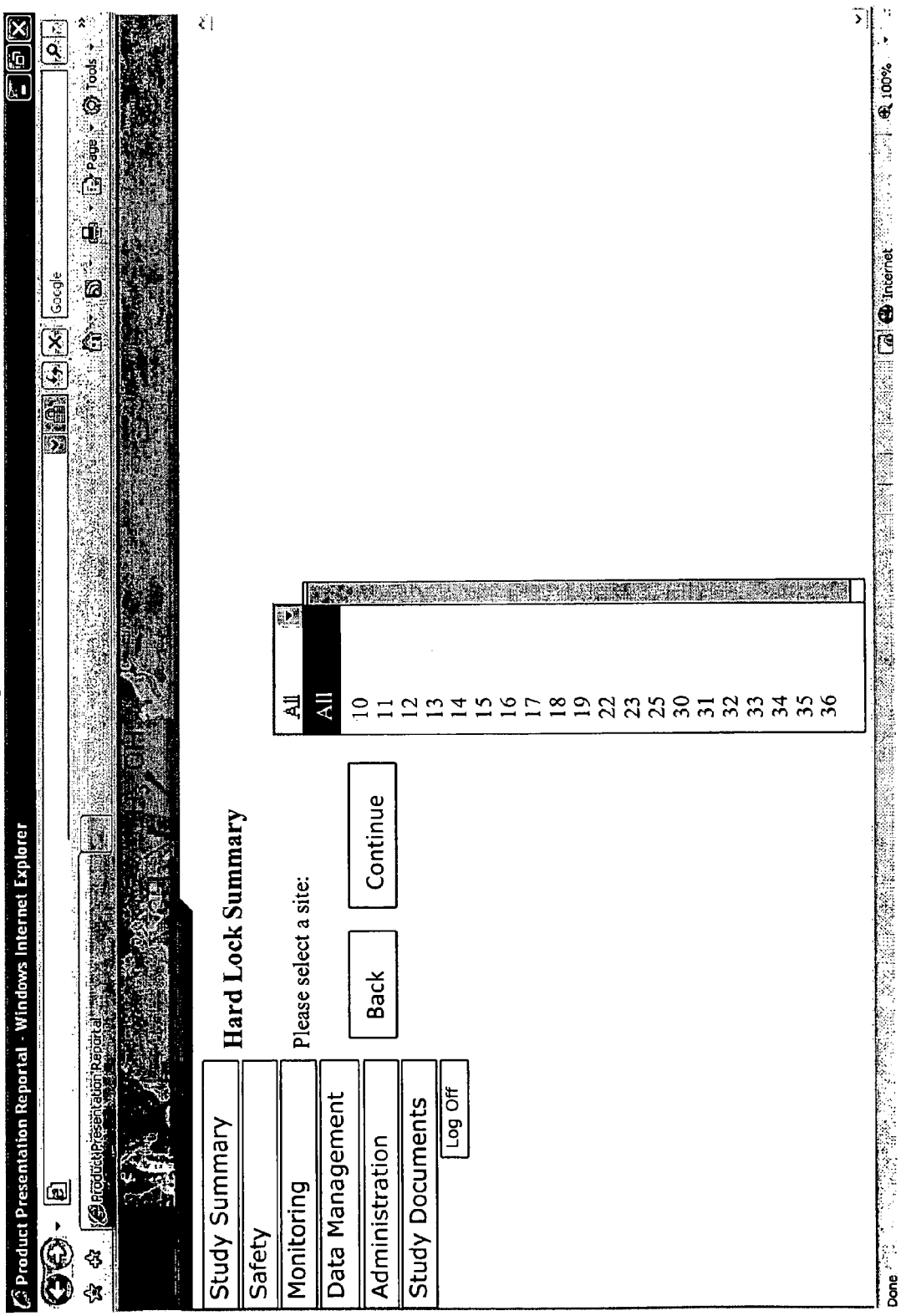

Another example of a type of lock is called a "hard lock." In this example, the criteria are set to include all CRFs up to a certain point in time. To view this report, the monitor elects the hard lock summary report (FIG. 8, item 2). Next the geographic region is selected (FIGS. 16 and 17) and the specific range of site in that region (FIG. 18). The summary is then displayed in FIG. 19. FIG. 19 item 1 shows the site number. In this example, the study design has two studies combined together. The first is called blinded study, and the second is called an open label study. The blinded study section is shown in FIG. 19, item 2, and the open label study section is shown in FIG. 19b, item 3. The lock criteria were defined as all CRFs and all visits for the blinded study, and all CRFs and all visits in the open label study up to a certain date. The site number link (FIG. 19, item 4) will display the site detail report (FIG. 20).

In this example, the site detail report is divided in two showing the blinded study components (FIG. 20, item 1), and the open label component (FIG. 20, item 2). The columns are identical to that of the soft lock detail (FIG. 13). There are also separate task lists for each of the two studies which may be selected by the links (FIG. 20, items 4 and 5). The patient detail is selected by the link on the patient number (item 3). FIGS. 21 and 22 depict each of the task lists for the blinded and open label studies, respectively.

Figure 23B:
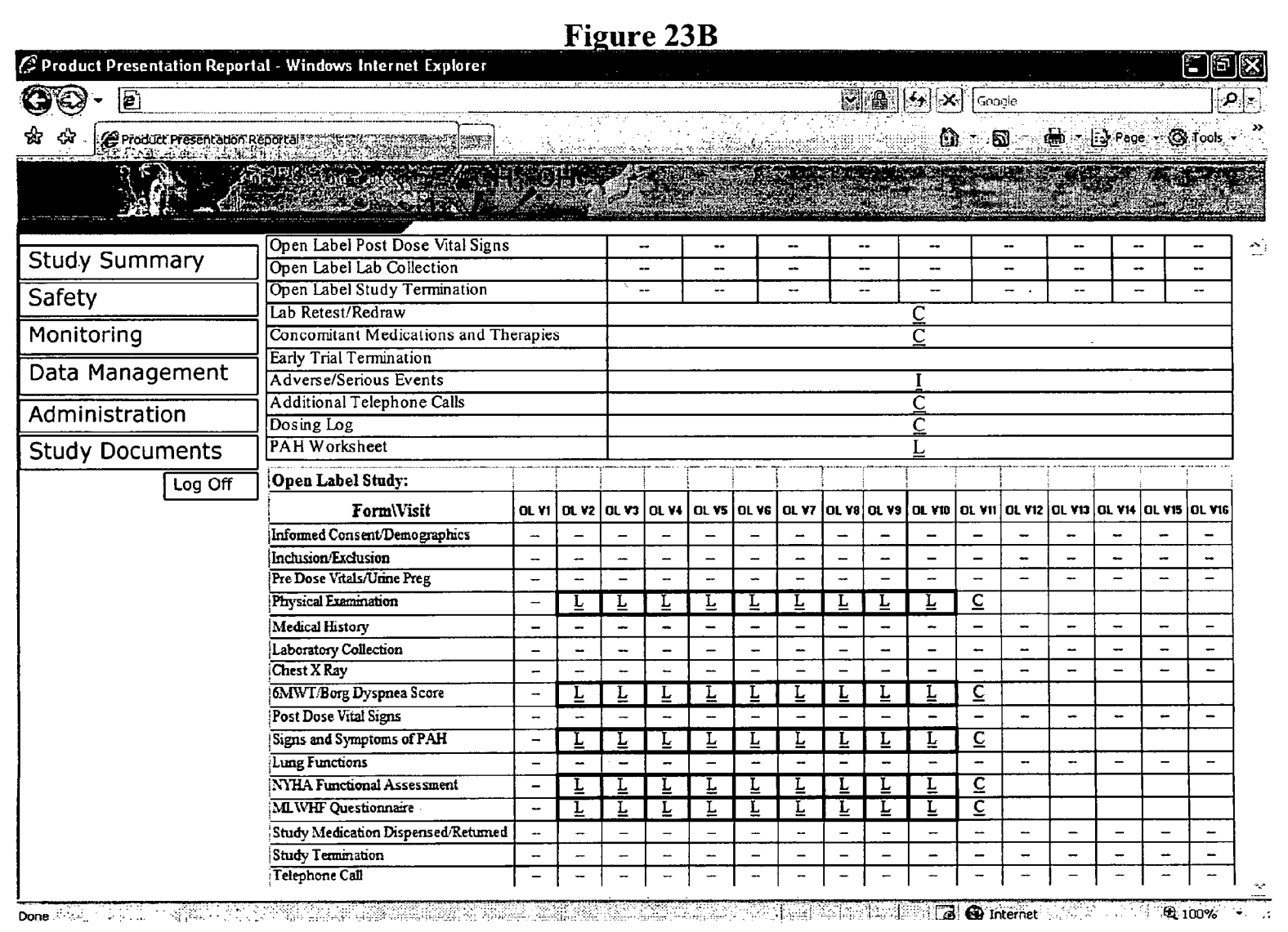
Figure 24:
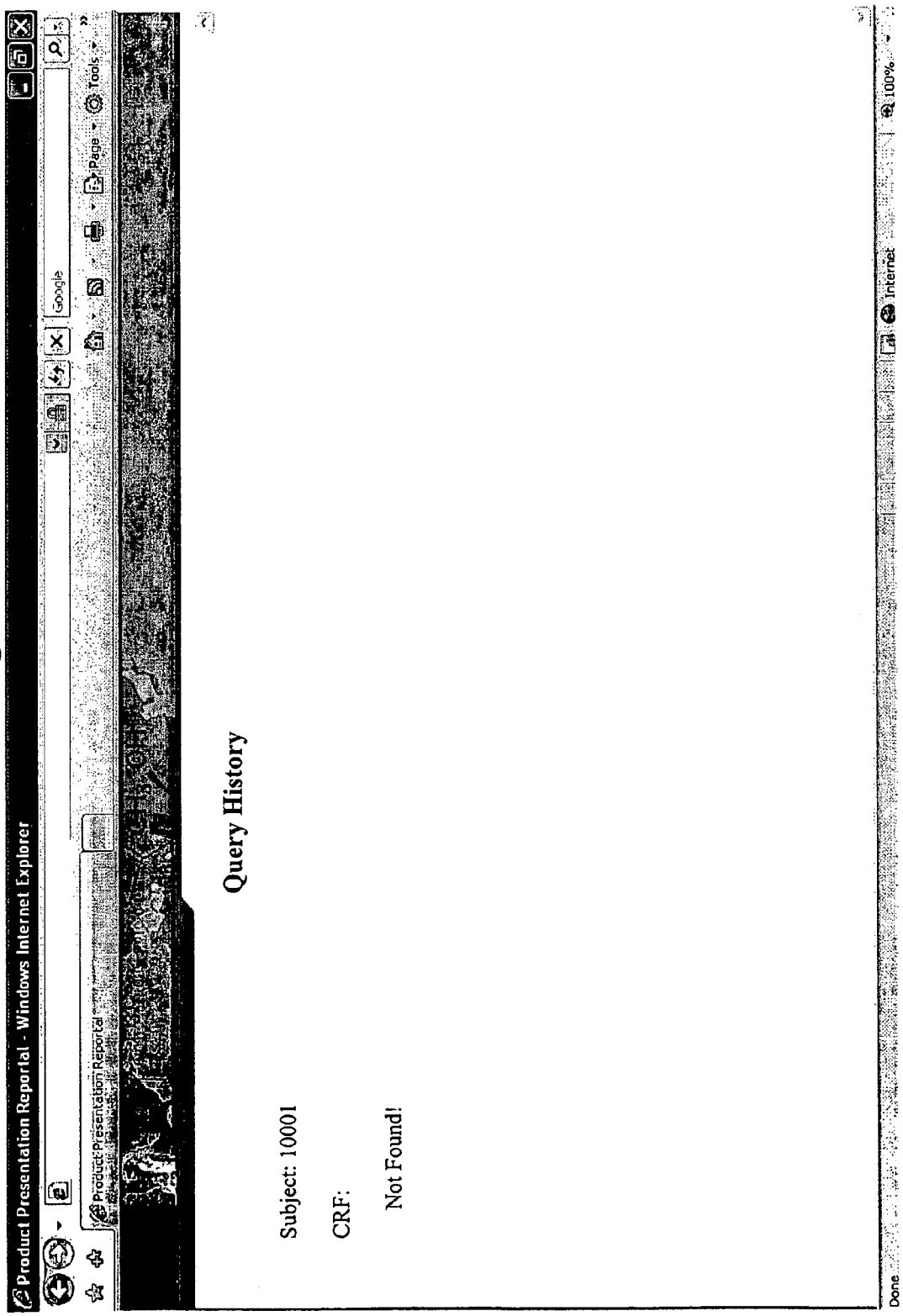

FIGS. 23a-23d show the detail for each patient. As in the soft lock, the CRF and visit grid is displayed. FIG. 23a shows the blinded grid and 23b shows the open label grid. FIGS. 23c-23d lists the coded adverse events recorded for the patient, as well as coded concomitant medications. In this example, the lock criteria required that each of these items be coded to a term in an industry standard medical dictionary. Specific CRFs (FIG. 25) may be viewed by selecting a link on the grid (FIG. 23a, item 1). A query history (FIG. 24) can be displayed by selecting the query history link (FIG. 25, item 1).

As discussed above, one preferred embodiment of the present invention is implemented via the source code in the Appendix.

The present invention may be implemented with any combination of hardware and software. If implemented as a computer-implemented apparatus, the present invention is implemented using means for performing all of the steps and functions described above.

The present invention can be included in an article of manufacture (e.g., one or more computer program products) having, for instance, computer useable media. The media has embodied therein, for instance, computer readable program code means for providing and facilitating the mechanisms of the present invention. The article of manufacture can be included as part of a computer system or sold separately.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An automated method of generating summary data regarding task items that must occur to achieve a database lock for a clinical trial study that is performed based on a previously defined clinical trial protocol, the clinical trial study being managed using (i) a processor, and (ii) a database in communication with the processor, the database including clinical trial data and the status of the data for a plurality of patients participating in the clinical trial study, the method comprising:

(a) electronically selecting at least one of the following criteria for a database lock:
   (i) one or more subsets of clinical trial data from a plurality of subsets of clinical trial data,
   (ii) one or more time frames or a time point in the study,
   (iii) one or more patient types, and
   (iv) a predefined number of patients;
(b) receiving in a processor the electronically selected criteria;
(c) defining in the processor clinical database lock criteria for the study from the electronically selected criteria;
(d) inputting into the processor:
   (i) the clinical database lock criteria for the study, and
   (ii) the clinical trial data and the status of the data, as retrieved from the database, for the plurality of patients participating in the clinical trial study as defined by the clinical database lock criteria; and
(e) automatically and programmatically generating via the processor summary data regarding task items that must occur to achieve the database lock as defined by the clinical database lock criteria for the study, wherein different summary data will be generated for different clinical database lock criteria.

2. The method of claim 1 further comprising selecting at least criteria (i) in step (a) wherein the criteria (i) further comprises specific clinical patient data of interest.

3. The method of claim 1 wherein the summary data includes the number of task items that must occur to achieve the database lock.

4. The method of claim 1 wherein the summary data provides information that allows for a determination of the number of clinical sites that have patients with uncompleted task items.

5. The method of claim 1 wherein the summary data provides information that allows for a determination of patients with uncompleted task items.

6. The method of claim 1 wherein the summary data is organized by types of uncompleted tasks.

7. The method of claim 1 further comprising selecting a plurality of the criteria in step (a).

8. The method of claim 1 further comprising selecting at least criteria (i)-(iii) in step (a).

9. An automated method of generating a list of task items that must occur to achieve a database lock for a clinical trial study that is performed based on a previously defined clinical trial protocol, the clinical trial study being managed using (i) a processor, and (ii) a database in communication with the processor, the database including clinical trial data and the status of the data for a plurality of patients participating in the clinical trial study, the method comprising:
   (a) electronically selecting at least one of the following criteria for a database lock:
      (i) one or more subsets of clinical trial data from a plurality of subsets of clinical trial data,
      (ii) one or more time frames or a time point in the study,
      (iii) one or more patient types, and
      (iv) a predefined number of patients;
   (b) receiving in a processor the electronically selected criteria;
   (c) defining in the processor clinical database lock criteria for the study from the electronically selected criteria;
   (d) inputting into the processor:
      (i) the clinical database lock criteria for the study, and
      (ii) the clinical trial data and the status of the data, as retrieved from the database, for the plurality of patients participating in the clinical trial study as defined by the clinical database lock criteria; and
   (e) automatically and programmatically generating via the processor a list of task items that must occur to achieve the database lock as defined by the clinical database lock criteria for the study, wherein a different list of task items will be generated for different clinical database lock criteria.

10. The method of claim 9 further comprising selecting at least criteria (i) in step (a) wherein the criteria (i) further comprises specific clinical patient data of interest.

11. The method of claim 9 wherein the list of task items includes locking a case report form.

12. The method of claim 9 wherein the list of task items includes identifying missing or incomplete case report forms.

13. The method of claim 9 wherein the list of task items includes identifying case report forms that have not been signed by authorized medical personnel.

14. The method of claim 9 wherein the list of task items includes identifying case report forms that include open queries.

15. The method of claim 9 further comprising selecting a plurality of the criteria in step (a).

16. The method of claim 9 further comprising selecting at least criteria (i)-(iii) in step (a).

17. An article of manufacture for generating a list of task items that must occur to achieve a database lock for a clinical trial study that is performed based on a previously defined clinical trial protocol, the clinical trial study being managed using (i) a processor, and (ii) a database in communication with the processor, the database including clinical trial data and the status of the data for a plurality of patients participating in the clinical trial study, the article of manufacture comprising a computer-readable medium encoded with computer-executable instructions for performing a method comprising:
   (a) electronically selecting at least one of the following criteria for a database lock:
      (i) one or more subsets of clinical trial data from a plurality of subsets of clinical trial data,
      (ii) one or more time frames or a time point in the study,
      (iii) one or more patient types, and
      (iv) a predefined number of patients;
   (b) receiving in a processor the electronically selected criteria;
   (c) defining in the processor clinical database lock criteria for the study from the electronically selected criteria;
   (d) inputting into the processor:
      (i) the clinical database lock criteria for the study, and
      (ii) the clinical trial data and the status of the data, as retrieved from the database, for the plurality of patients participating in the clinical trial study as defined by the clinical database lock criteria; and
   (e) automatically and programmatically generating via the processor a list of task items that must occur to achieve the database lock as defined by the clinical database lock criteria for the study, wherein a different list of task items will be generated for different clinical database lock criteria.

18. The article of manufacture of claim 17 further comprising selecting a plurality of the criteria in step (a).

19. The article of manufacture of claim 17 further comprising selecting at least criteria (i)-(iii) in step (a).

* * * * *